United States Patent
Trotter et al.

(10) Patent No.: US 8,278,317 B2
(45) Date of Patent: Oct. 2, 2012

(54) POTASSIUM CHANNEL INHIBITORS

(75) Inventors: B. Wesley Trotter, Glenside, PA (US);
Kausik K. Nanda, Norristown, PA (US);
Scott E. Wolkenberg, Jenkintown, PA (US); M. Brad Nolt, Bluebell, PA (US);
David Wisnoski, Quakertown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1290 days.

(21) Appl. No.: 11/988,393

(22) PCT Filed: Jul. 18, 2006

(86) PCT No.: PCT/US2006/027530
§ 371 (c)(1),
(2), (4) Date: Jan. 7, 2008

(87) PCT Pub. No.: WO2007/015775
PCT Pub. Date: Feb. 8, 2007

(65) Prior Publication Data
US 2009/0124665 A1    May 14, 2009

Related U.S. Application Data

(60) Provisional application No. 60/701,801, filed on Jul. 22, 2005.

(51) Int. Cl.
*A61K 31/4406* (2006.01)
*A61K 31/4439* (2006.01)
*C07D 401/02* (2006.01)
*C07D 413/02* (2006.01)
*C07D 213/46* (2006.01)

(52) U.S. Cl. .............. 514/277; 514/340; 546/268.4; 546/269.1; 546/271.4; 546/342

(58) Field of Classification Search .............. 514/340, 514/277; 546/342, 269.1, 268.4, 271.4
See application file for complete search history.

(56) References Cited

U.S. PATENT DOCUMENTS
2003/0225099 A1    12/2003  Peukert et al.

OTHER PUBLICATIONS

Vippagunta et al., Cyrstalline Solids, 2001, Advanced Drug Delivery Reviews, 48, pp. 3-26.*
Anthony R. West, Solid Solutions, 1988, Solid State Chemistry and its applications, pp. 358 & 365.*
Chawla et al., Challenges in Polymorphism of Pharmaceuticals, CRIPS, vol. 5, No. 1, Jan.-Mar. 2004, pp. 9-12.*
Newman et al., Solid-state analysis of the active pharmaceutical ingredient in drug products, DDT, vol. 8, No. 19, Oct. 2003, pp. 898-905.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Snyder, "Chromatographic behavior of diastereoisomers", J. of Chromatography (1986), vol. 354, pp. 107-118.
Decher, et al. "Molecular Basis for Kv1.5 Channel Block", Journal of Biological Chemistry, Jan. 2, 2004, vol. 279, No. 1, pp. 394-400, especially abstract, p. 399, Figure 7.
Doyle, et al. "The Structure of the Potassium Channel: Molecular Basis of Potassium Conduction and Selectivity", Science, Apr. 3, 1998, vol. 280, pp. 69-77, especially p. 69, p. 72, Table 1.

* cited by examiner

*Primary Examiner* — Kristin Bianchi
(74) *Attorney, Agent, or Firm* — Richard S. Parr; Catherine D. Fitch

(57) ABSTRACT

The present invention relates to compounds having the structure (I) useful as potassium channel inhibitors to treat cardiac arrhythmias, and the like.

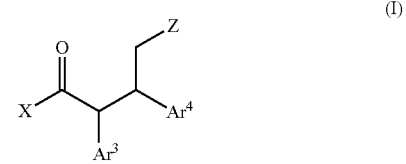

4 Claims, 1 Drawing Sheet

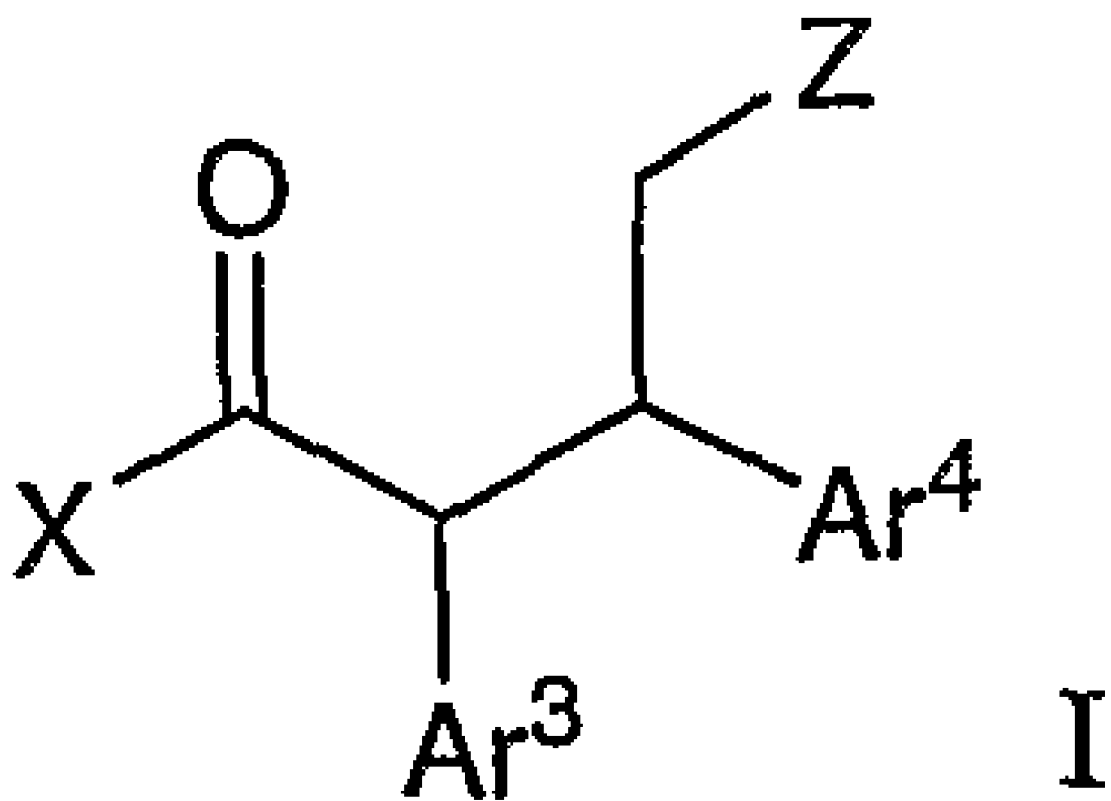
I

POTASSIUM CHANNEL INHIBITORS

CROSS REFERENCE TO RELATED APPLICATION

This application is a U.S. National Phase application under 35 U.S.C. §371 of PCT Application No. PCT/US2006/027530, filed Jul. 18, 2006, which claims priority under 35 U.S.C. §119(e) from U.S. Provisional Application Ser. No. 60/701,801, filed Jul. 22, 2005.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like.

Atrial fibrillation (AF) is the most common sustained cardiac arrhythmia in clinical practice and is likely to increase in prevalence with the aging of the population. While AF is rarely fatal, it can impair cardiac function and lead to complications such as the development of congestive heart failure, thromboembolism, or ventricular fibrillation.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation*, 102:2665-2670), but pose an unacceptable risk of potentially lethal ventricular proarrhythmia and thus may increase mortality (Pratt, C M, Moye, L A, *Am J. Cardiol.*, 65:20B-29B, 1990; Waldo et al, *Lancet*, 348:7-12, 1996; Torp-Pedersen et al, *Expert Opin. Invest. Drugs*, 9:2695-2704, 2000). These observations demonstrate a clear unmet medical need to develop safer and more efficacious drugs for the treatment of atrial arrhythmias. Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation*, 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest Drugs*, 9:2695-2704, 2000). However, these agents have the major liability of an enhanced risk of proarrhythmia at slow heart rates.

The ultrarapid delayed rectifier $K^+$ current, $I_{Kur}$, has been observed specifically in human atrium and not in ventricle. The molecular correlate of $I_{Kur}$ in the human atrium is the potassium channel designated Kv1.5. $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic after depolarizations and acquired long QT syndrome observed during treatment with current Class III drugs.

Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

The invention concerns compounds of formula I which antagonize the Kv1.5 potassium channel:

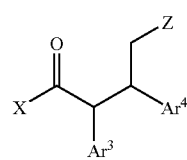

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention concerns compounds of formula I which antagonize the Kv1.5 potassium channel:

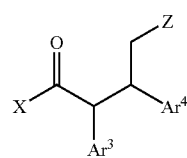

wherein:
X is —NR¹R² or —OR²;
Z is selected from the group consisting of
a) —NHC(O)$C_{1-6}$ alkylene-A,
b) —NHC(O)$C_{1-6}$ alkyl,
c) —NHC(O)NHC$_{0-6}$ alkylene-A,
d)

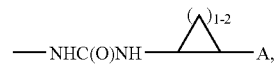

e) —NHC(O)NHC$_{1-6}$ alkyl,
f) —NHSO$_2$C$_{0-6}$ alkylene-A,
g) —NHSO$_2$C$_{2-6}$ alkenyl-A,
h) —NHSO$_2$C$_{1-16}$ alkyl,
i) —C(O)NHC$_{0-6}$ alkylene-A,
j) —C(O)NHC$_{1-7}$ alkyl,
k) —C(O)NH$_2$,
l) —C(O)OC$_{1-6}$ alkyl,
m) —C(O)N(C$_{1-6}$ alkyl)$_2$,
n) —Y,
o) —C(O)NHNH$_2$,
p) —C(O)NHC$_{1-6}$ alkylene-S—C$_{1-6}$ alkyl
q) —C(O)NHC$_{1-6}$ alkylene-O—C$_{1-6}$ alkyl r) —C(O)NHC$_{1-6}$ alkylene-C(O)O—C$_{1-6}$ alkyl
s) —CN,
t) —C$_{1-6}$ alkyl, and
u) —NHC(O)OC$_{1-6}$ alkyl;
where Y is
a 5-membered unsaturated monocyclic ring with 1, 2, 3 or 4 heteroatom ring atoms selected from the group consisting of N, O and S, wherein the point of attachment is a carbon atom, said ring is unsubstituted or mono-substituted with R$^4$, wherein the substituent is on a carbon atom or a nitrogen atom;
A is selected from the group consisting of
1) an aryl ring,
2) a saturated C$_{3-8}$ monocyclic, or saturated or unsaturated C$_{7-12}$ bicyclic, carbocyclic ring system,
3) a heteroaryl ring, wherein the point of attachment to the heteroaryl ring is a carbon atom, and the heteroaryl ring is selected from the group consisting of:
a) a 5-membered unsaturated monocyclic ring with 1, 2, 3, or 4 heteroatom ring atoms selected from the group consisting of N, O or S,
b) a 6-membered unsaturated monocyclic ring with 1, 2, 3, or 4 heteroatom ring atoms selected from the group consisting of N, O or S, and
c) an 8-, 9- or 10-membered unsaturated bicyclic ring with 1, 2, 3, or 4 heteroatom ring atoms selected from the group consisting of N, O or S, and
4) a 4-6 membered saturated heterocyclic ring with 1, 2 or 3 heteroatom ring atoms selected from the group consisting of N, O and S, wherein the point of attachment to the heterocyclic ring is a carbon atom,
said aryl, carbocyclic, heteroaryl, or saturated heterocyclic ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl or heterocyclic ring atom is unsubstituted or substituted with oxo, said heteroaryl ring R$^4$ substitutions being on one or more heteroaryl ring carbon atoms;
R$^1$ and R$^2$ are independently selected from the group consisting of
1) hydrogen,
2) unsubstituted or substituted C$_{1-6}$ alkyl,
3) unsubstituted or substituted C$_{3-10}$ cycloalkyl,
4) unsubstituted or substituted aryl,
5) unsubstituted or substituted heterocycle,
6) CF$_3$,
7) unsubstituted or substituted C$_{2-6}$ alkenyl, and
8) unsubstituted or substituted C$_{2-6}$ alkynyl;
Ar$^3$ and Ar$^4$ are independently selected from the group consisting of
1) an aryl ring, and
2) a heteroaryl ring, wherein the point of attachment to the heteroaryl ring is a carbon atom, and the heteroaryl ring is selected from the group consisting of:
a) a 5-membered unsaturated monocyclic ring with 1, 2, 3, or 4 heteroatom ring atoms selected from the group consisting of N, O or S,
b) a 6-membered unsaturated monocyclic ring with 1, 2, 3, or 4 heteroatom ring atoms selected from the group consisting of N, O or S, and
c) an 8-, 9- or 10-membered unsaturated bicyclic ring with 1, 2, 3, or 4 heteroatom ring atoms selected from the group consisting of N, O or S,
said aryl and heteroaryl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl or heterocyclic ring atom is unsubstituted or substituted with oxo, said heteroaryl ring R$^4$ substitutions being on one or more heteroaryl ring carbon atoms; and
R$^4$, in each instance in which it appears, is independently selected from the group consisting of
1) hydrogen,
2) halogen,
3) aryl,
4) C$_{1-6}$ alkyl,
5) C$_{1-6}$ alkoxy,
6) CN,
7) SO$_2$NH$_2$,
8) SO$_2$NHC$_{1-6}$ alkyl,
9) SO$_2$N(C$_{1-6}$ alkyl)$_2$,
10) CONH$_2$,
11) OH,
12) OC$_{1-6}$ haloalkyl, and
13) heteroaryl.

An embodiment of the invention is a compound wherein X is —NR$^1$R$^2$.

A preferred embodiment of the invention is a compound wherein R$^1$ and R$^2$ are independently selected from the group consisting of unsubstituted or substituted C$_{1-6}$ alkyl.

A more preferred embodiment of the invention is a compound wherein Ar$^3$ and Ar$^4$ are independently selected from the group consisting of
1) an aryl ring, and
2) a heteroaryl ring, wherein the point of attachment to the heteroaryl ring is a carbon atom, and the heteroaryl ring is a 6-membered unsaturated monocyclic ring with 1, 2, 3, or 4 heteroatom ring atoms selected from the group consisting of N, O or S,
said aryl and heteroaryl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl ring atom is unsubstituted or substituted with oxo, said heteroaryl ring R$^4$ substitutions being on one or more heteroaryl ring carbon atoms.

An even more preferred embodiment of the invention is a compound wherein Z is selected from the group consisting of

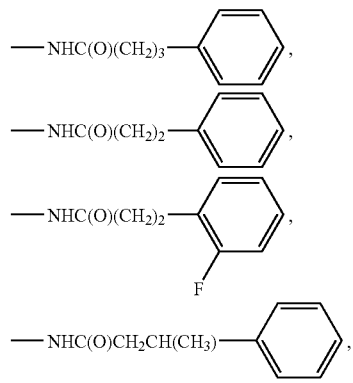

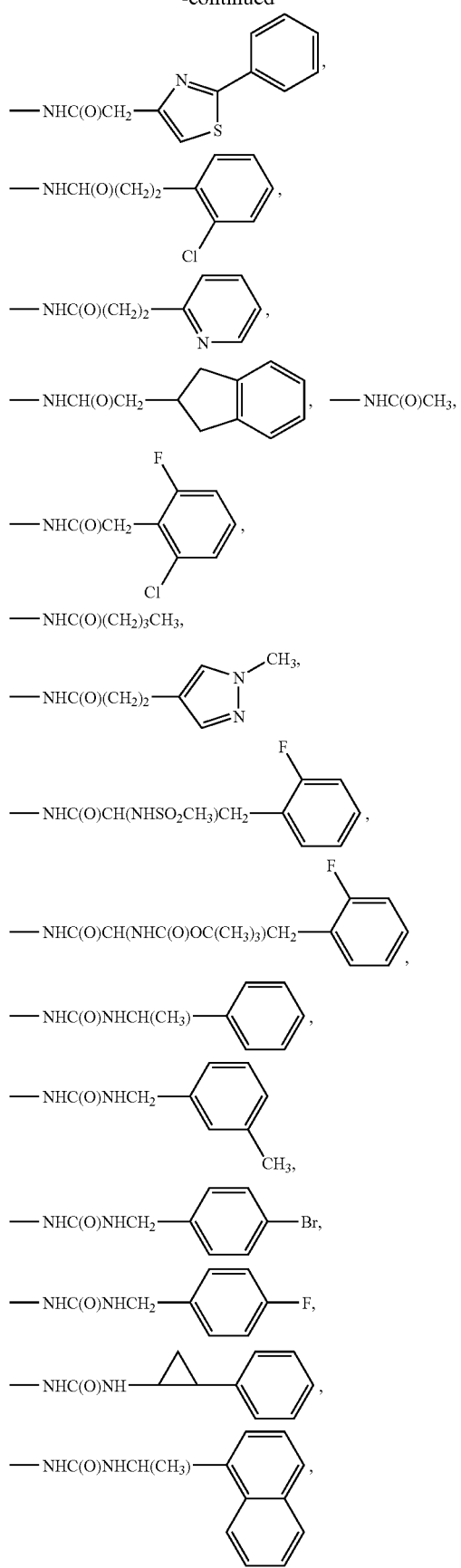
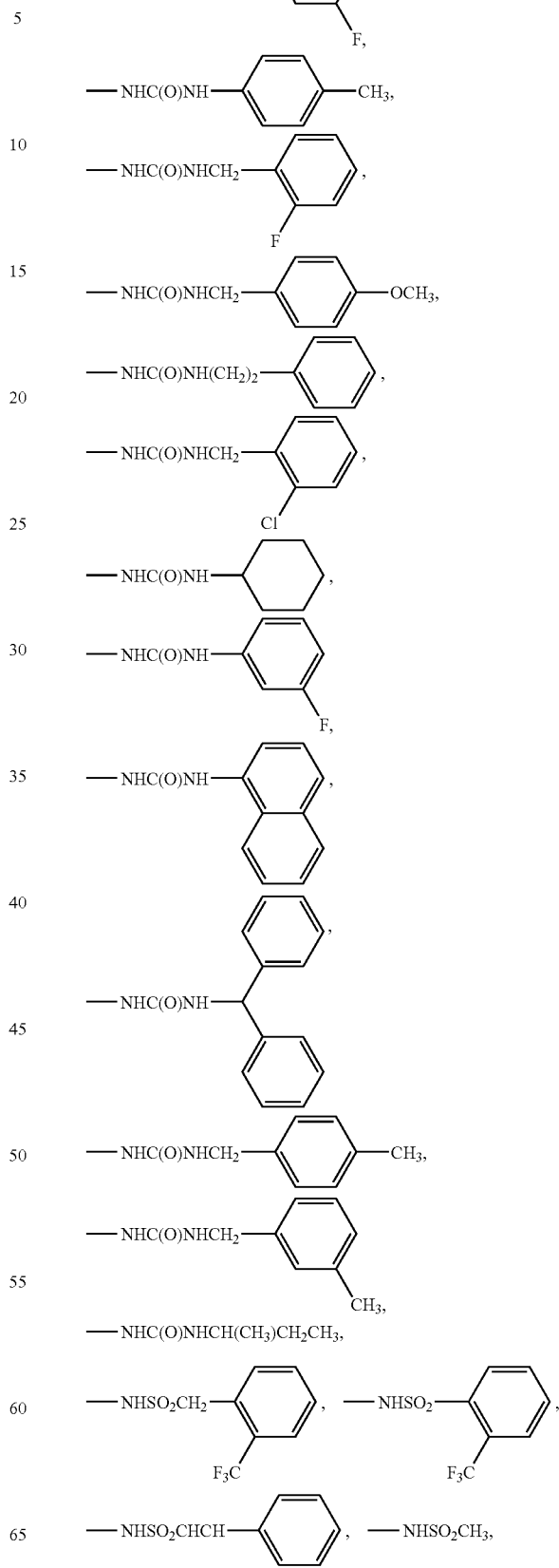

-continued
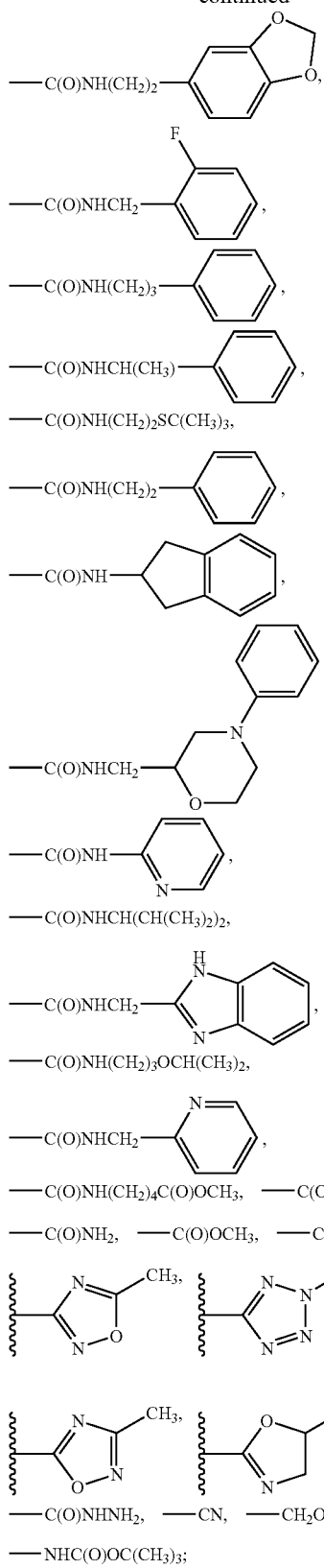
$R^1$ is —CH(CH$_3$)$_2$;
$R^2$ is —CH(CH$_3$)$_2$;
Ar$^3$ is selected from the group consisting of
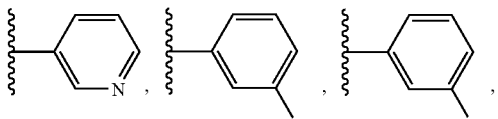
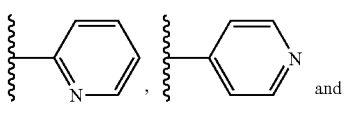
; and
Ar$^4$ is selected from the group consisting of
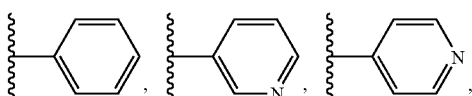
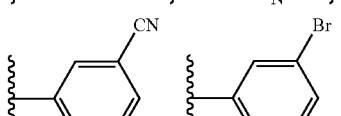
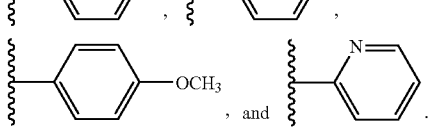
An example of a compound of this even more preferred embodiment is a compound, or a pharmaceutically acceptable salt thereof, selected from the group consisting of
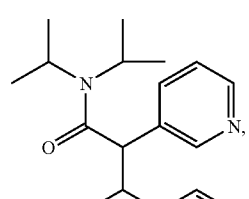
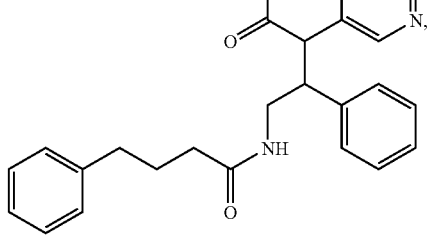
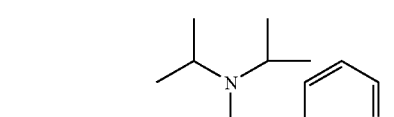
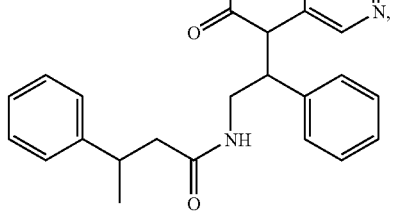

-continued
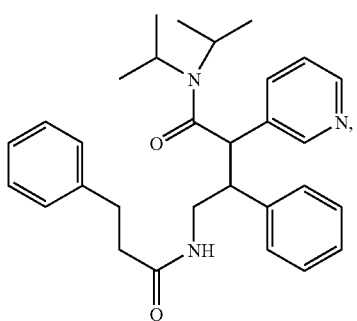
3
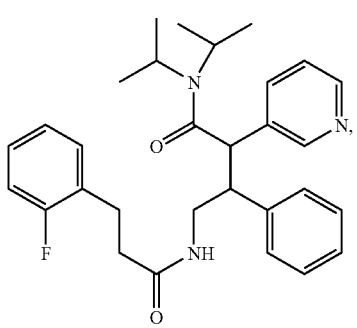
4
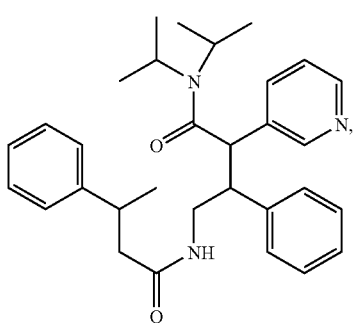
5
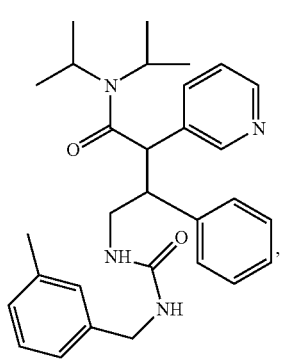
6
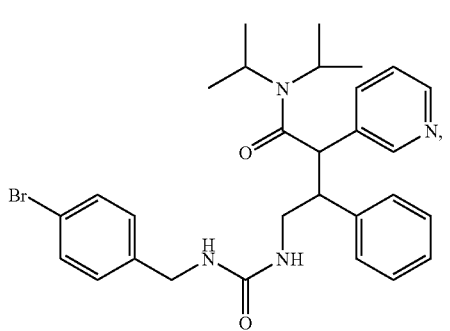
7
-continued
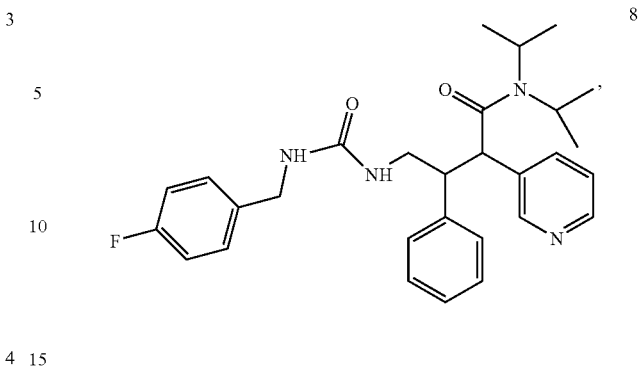
8
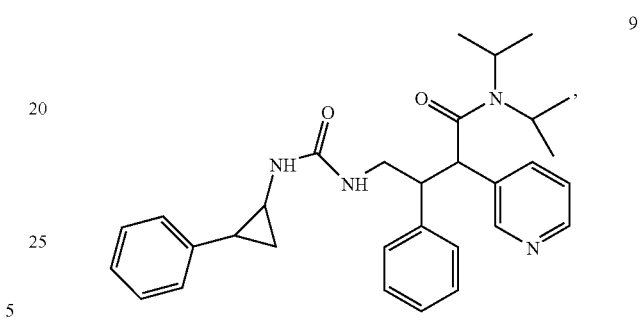
9
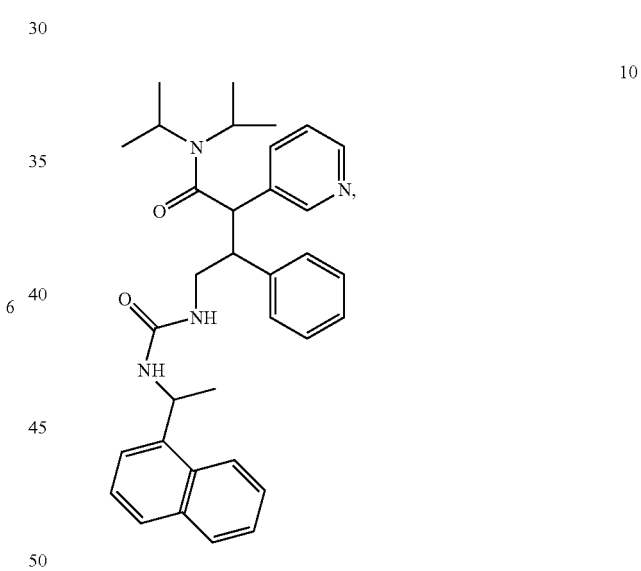
10
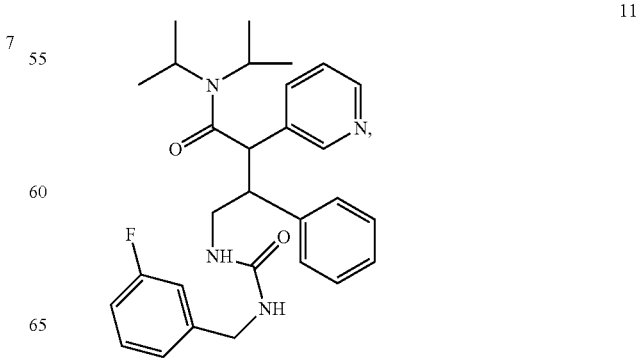
11

-continued
11
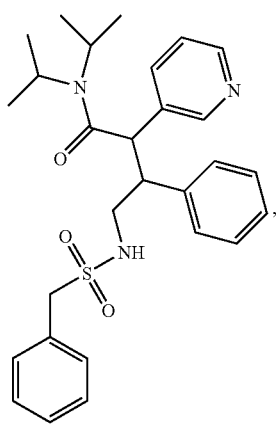
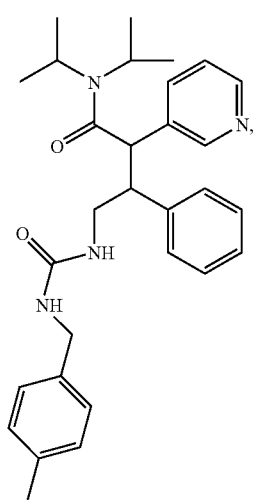
13
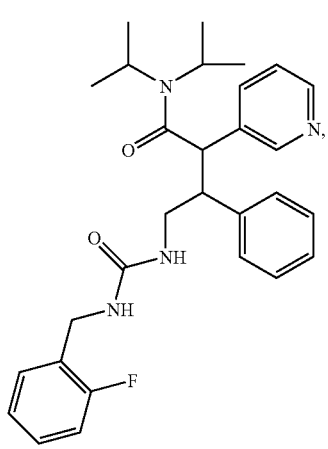
14
-continued
12
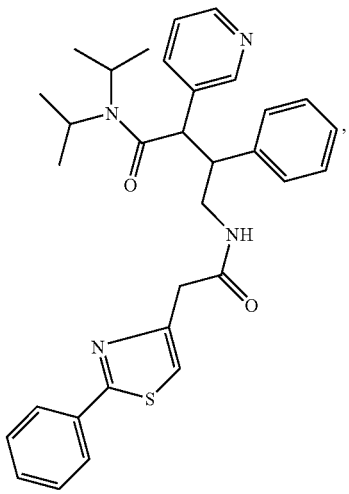
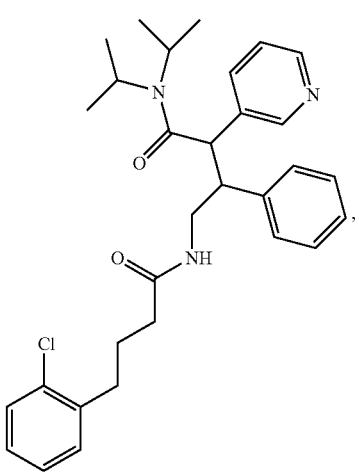
15
16
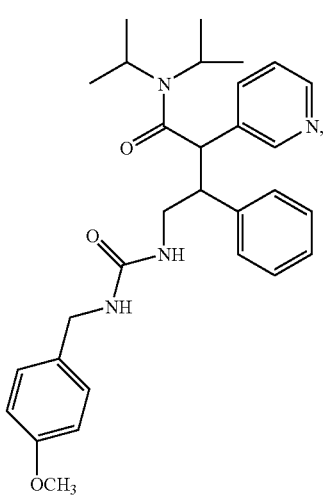
17

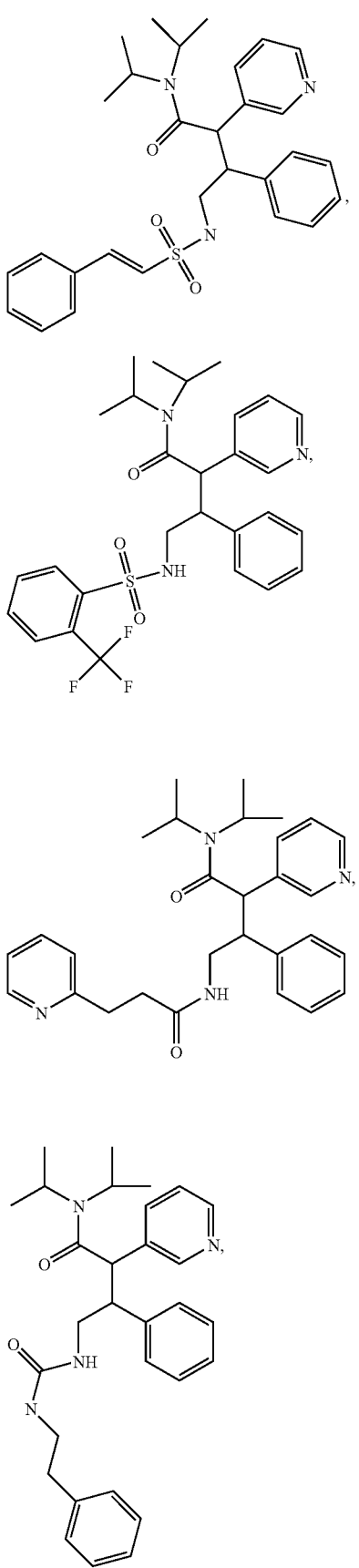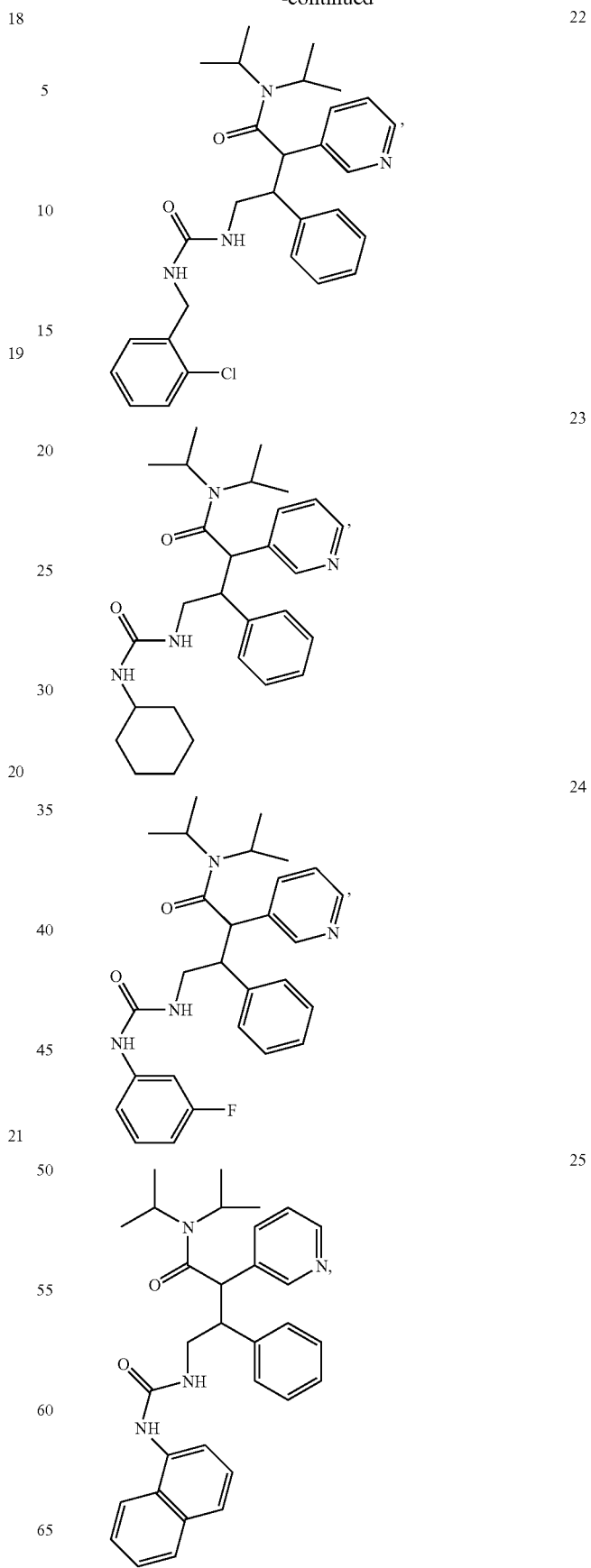

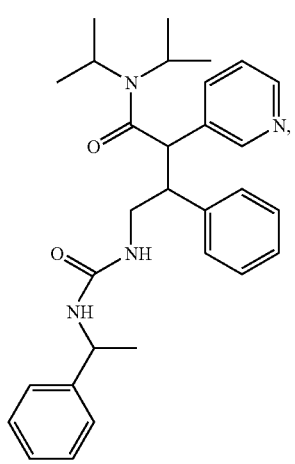
26
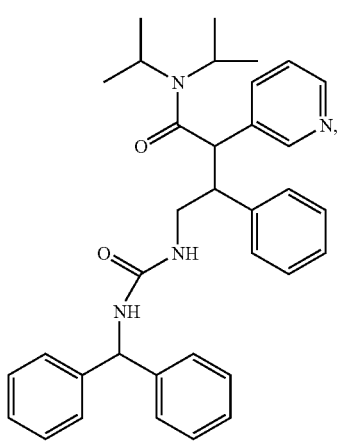
27
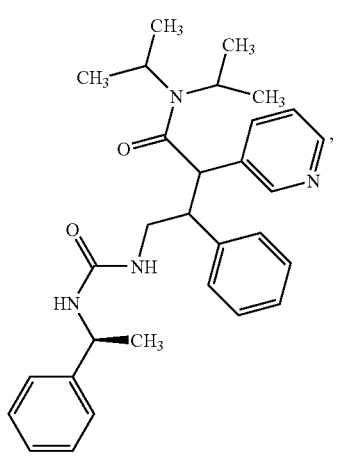
28
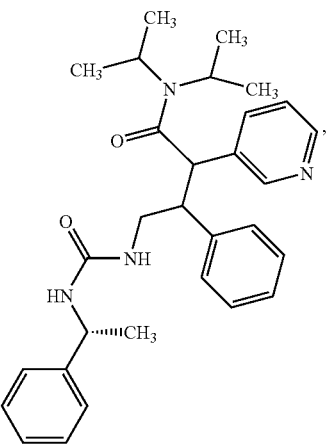
29
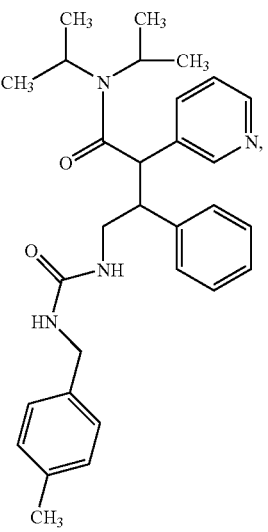
30
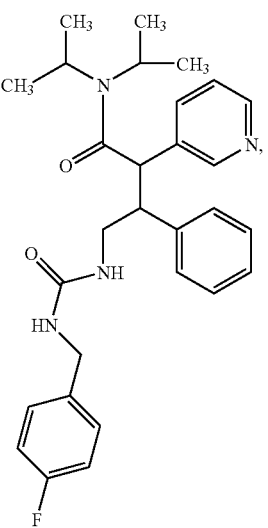
31

32
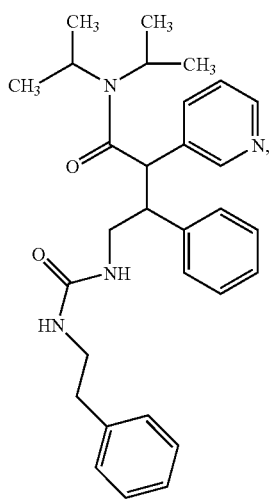
33
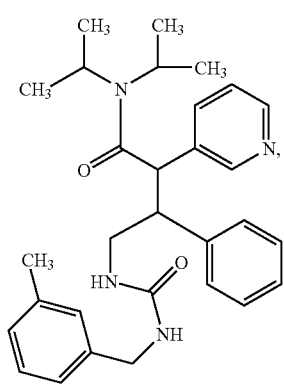
34
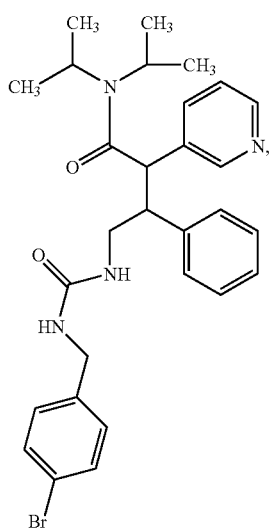
35
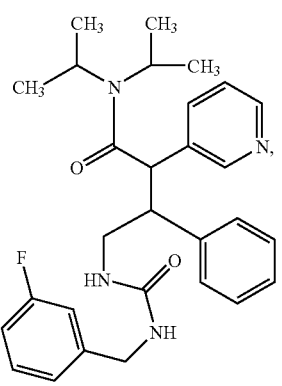
36
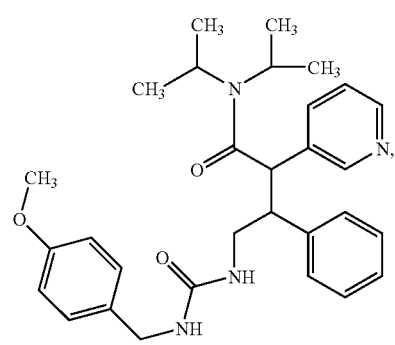
37
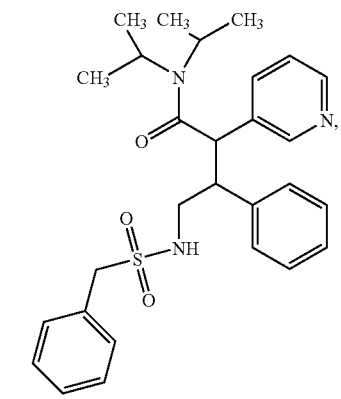
38
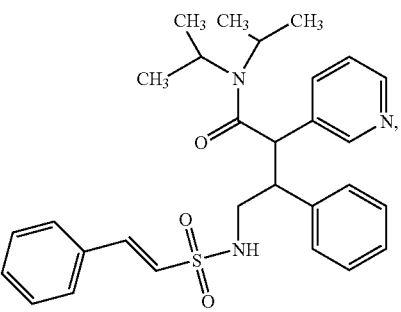

39
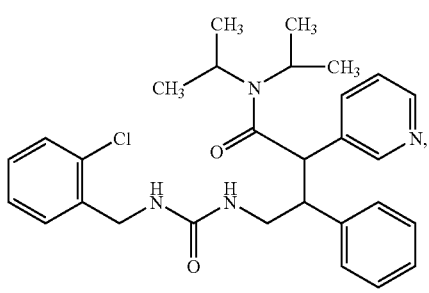
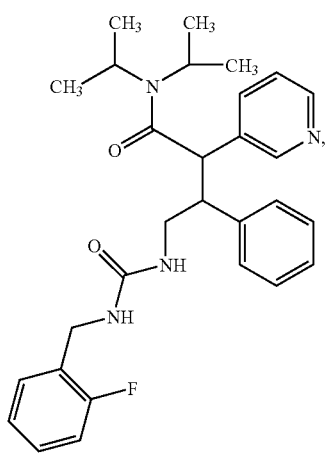
42
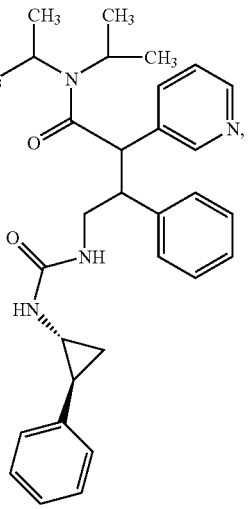
40
43
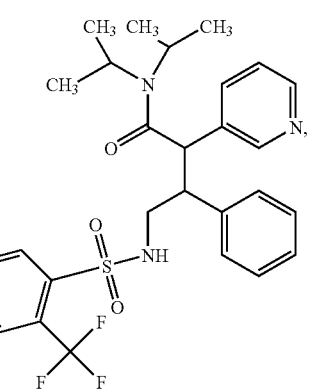
41
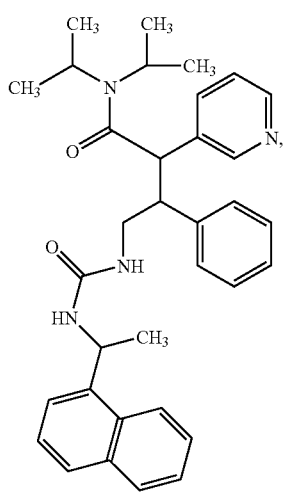
44
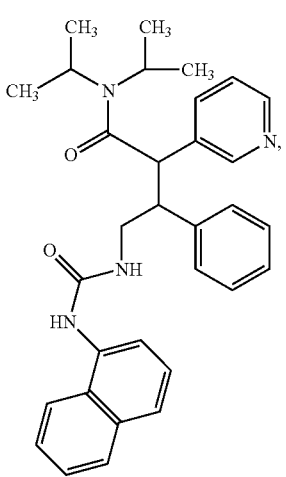

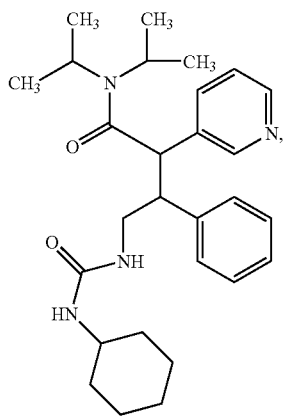
45
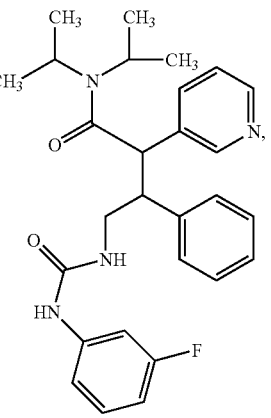
48
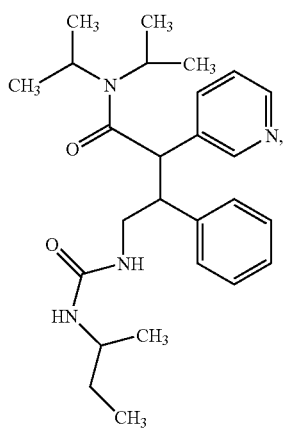
46
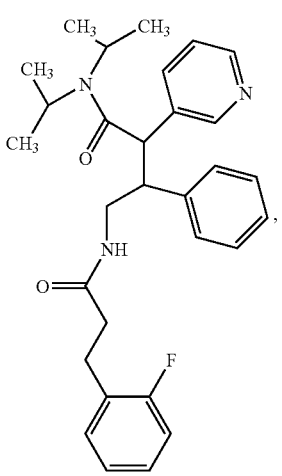
49
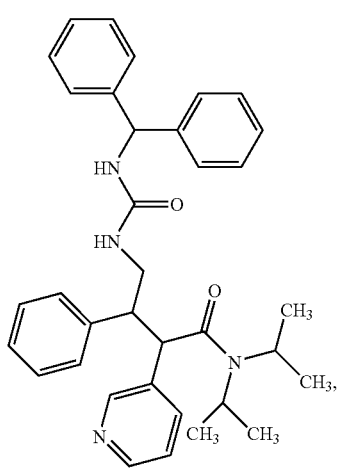
47
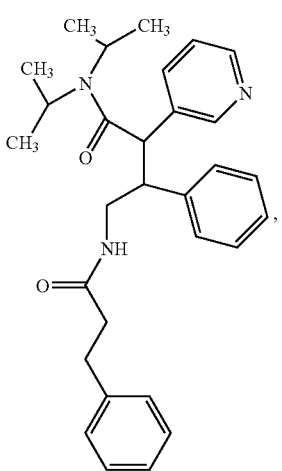
50

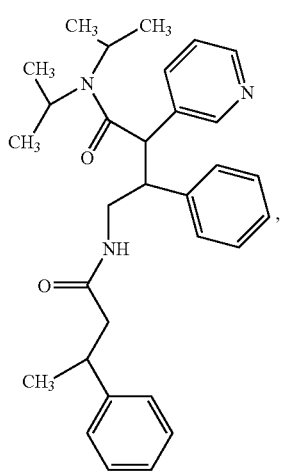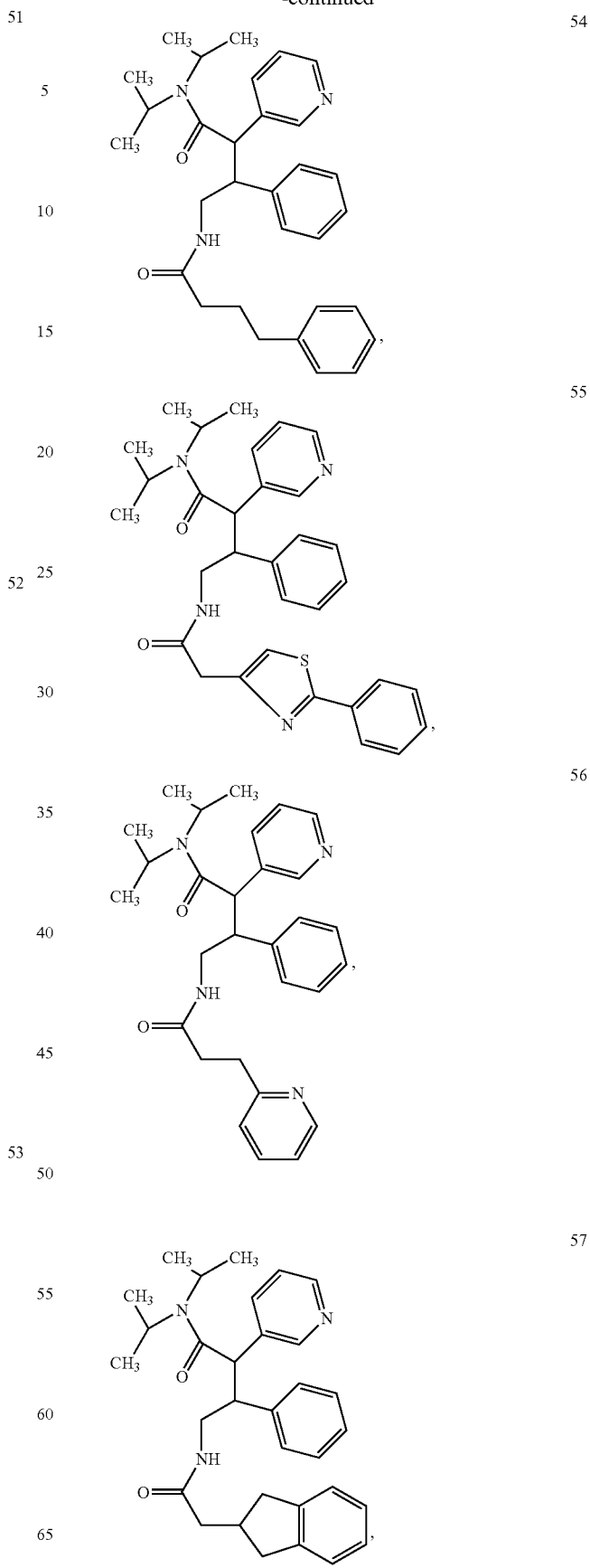

58
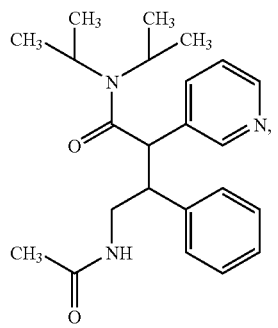
59
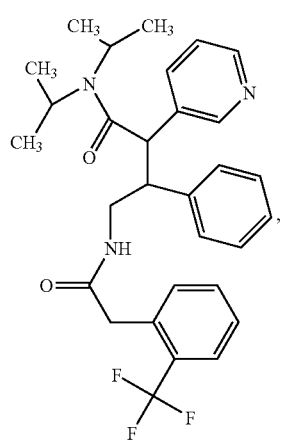
60
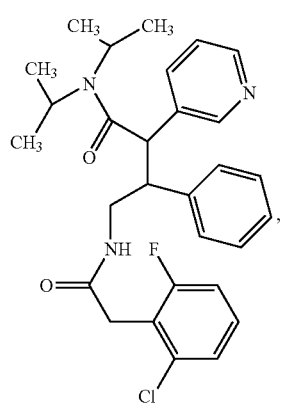
61
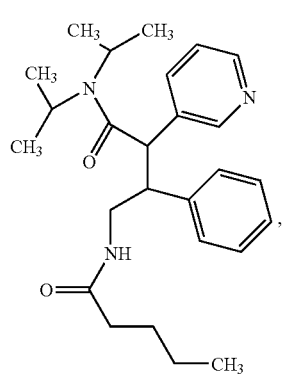
62
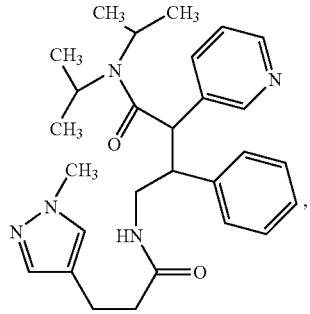
63
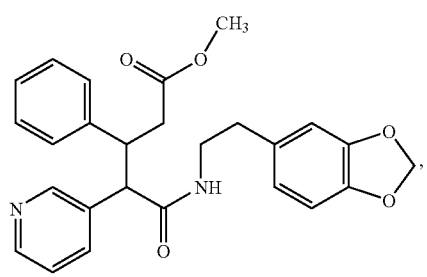
64
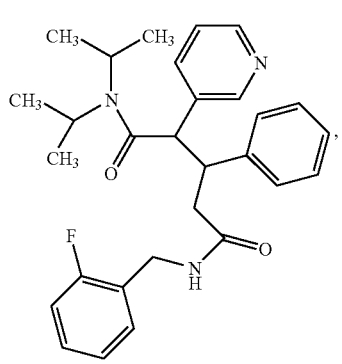
65
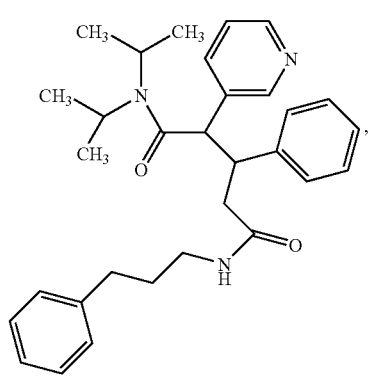
66
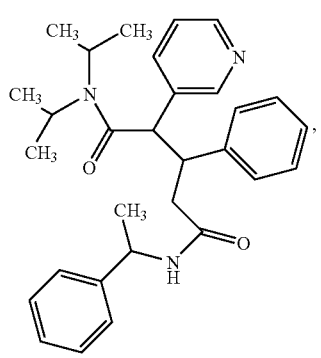

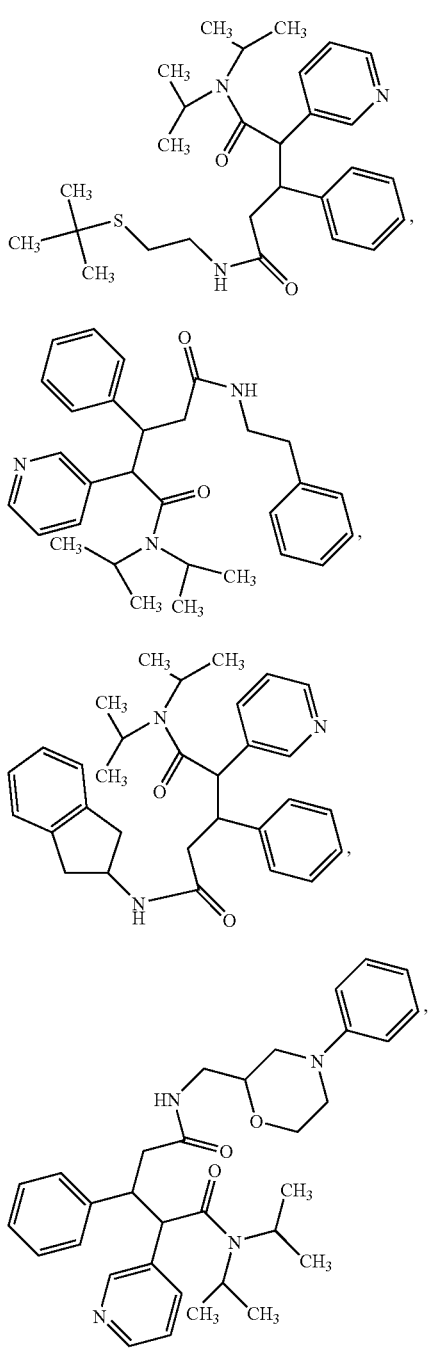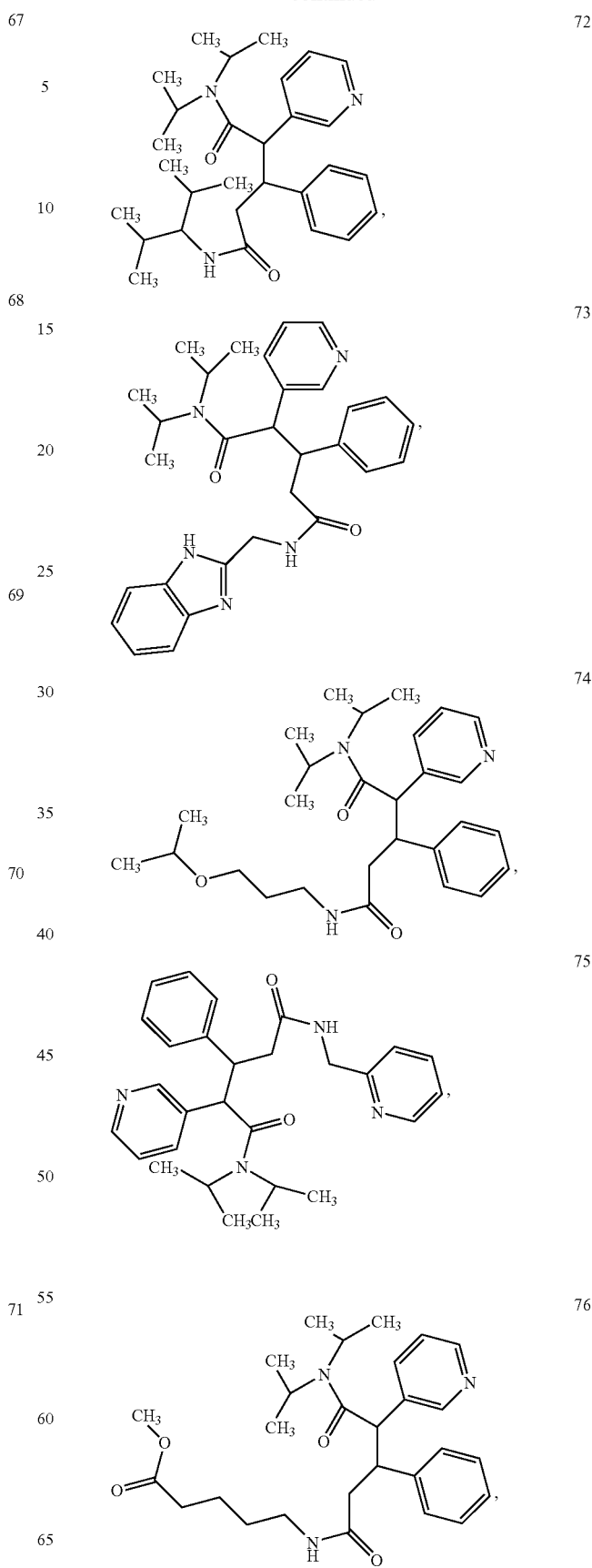

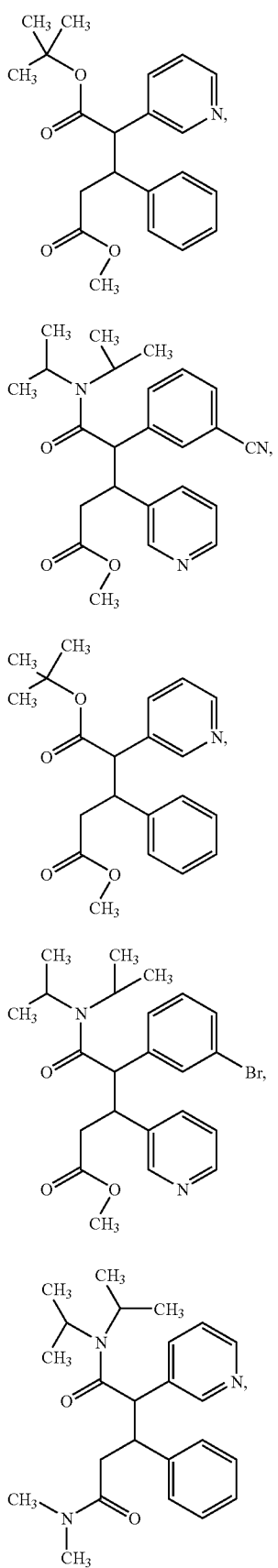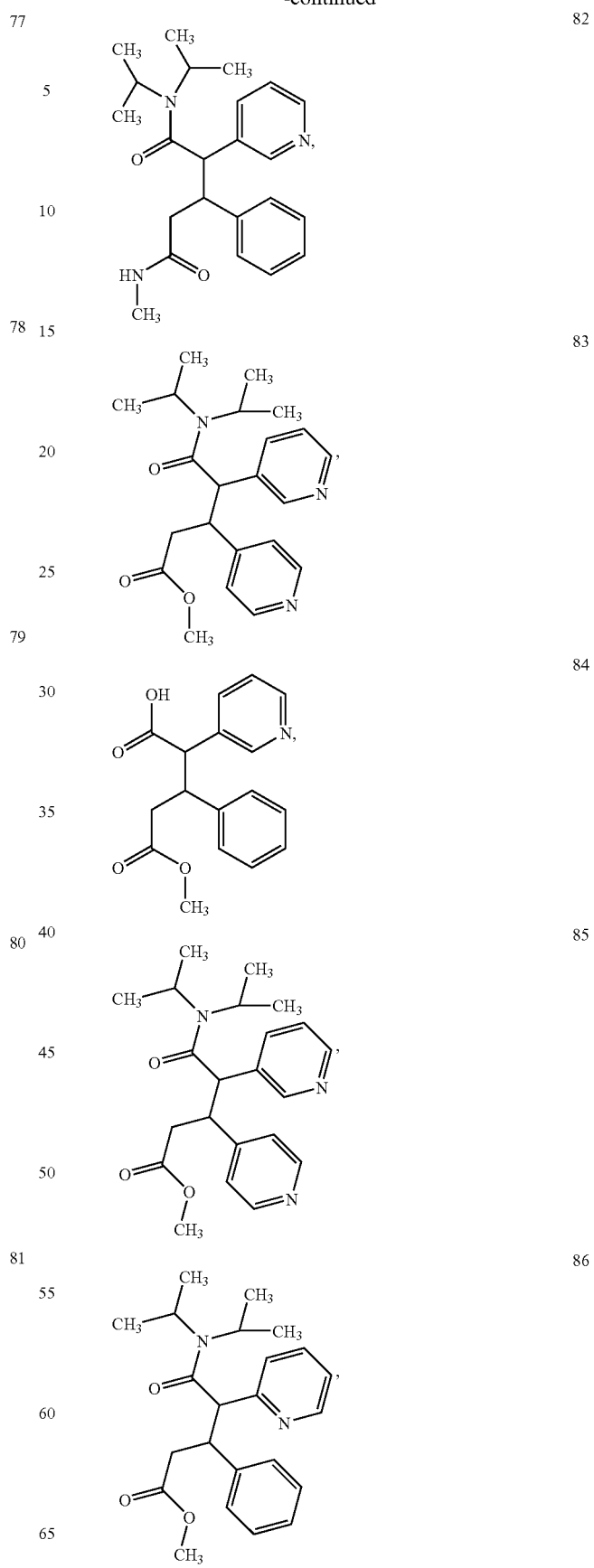

87
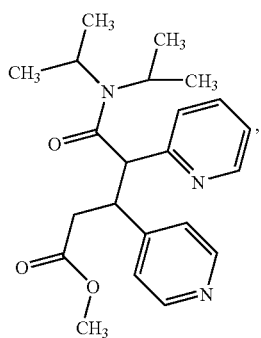
88
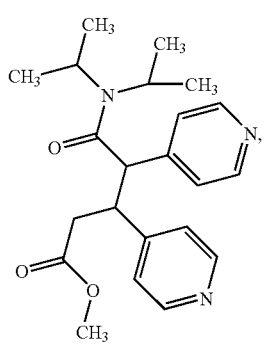
89
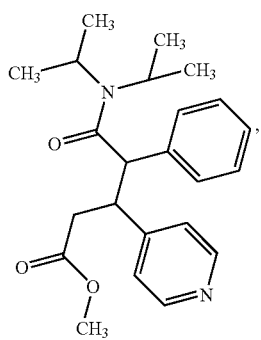
90
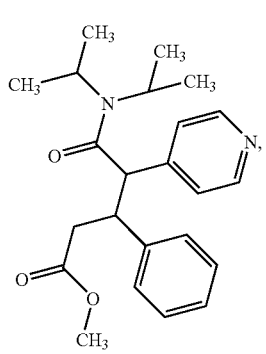
91
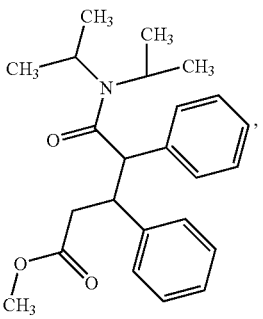
92
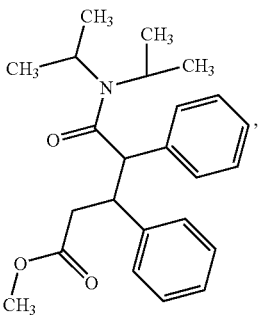
93
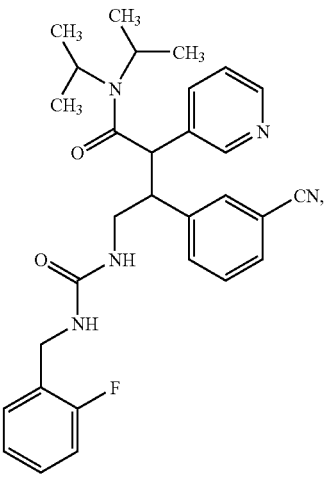
94
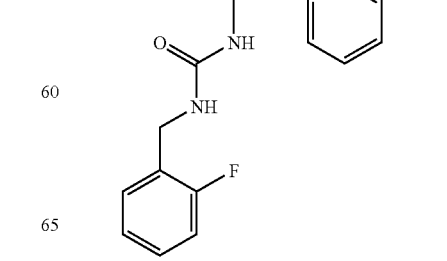

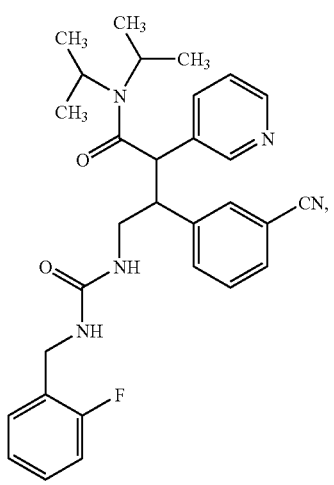
95
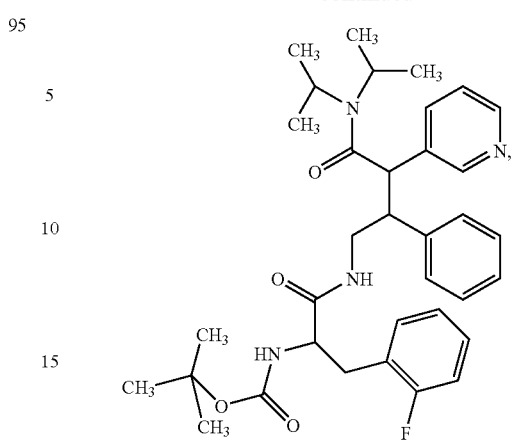
98
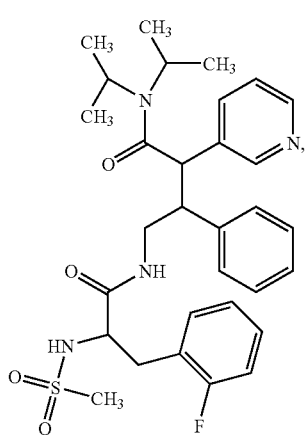
96
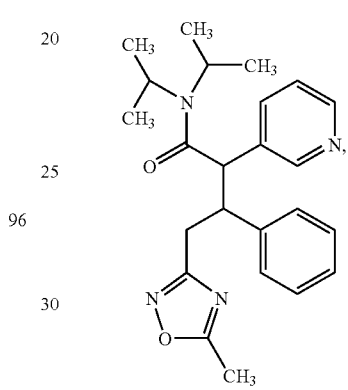
99
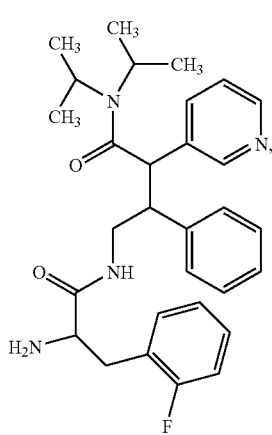
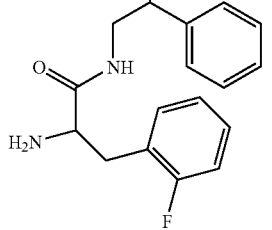
97
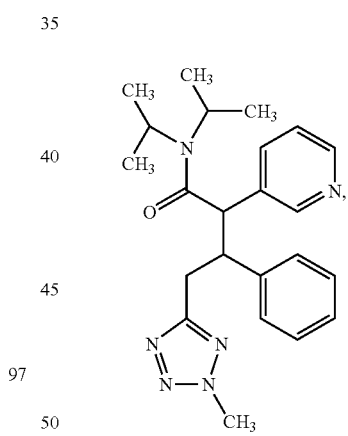
100
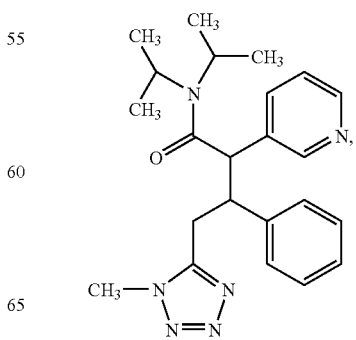
101

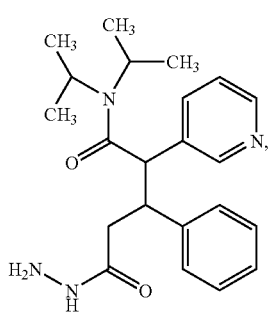
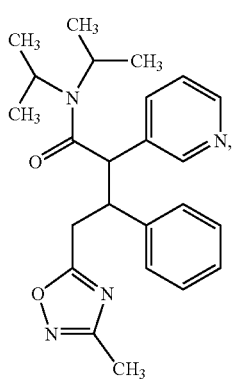
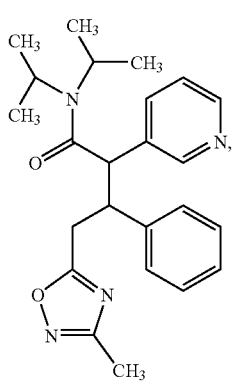
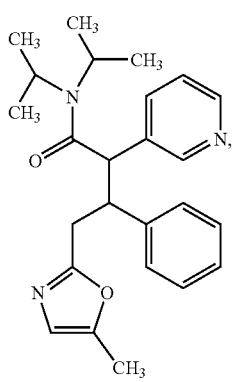
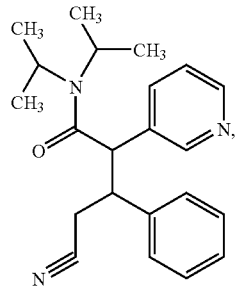
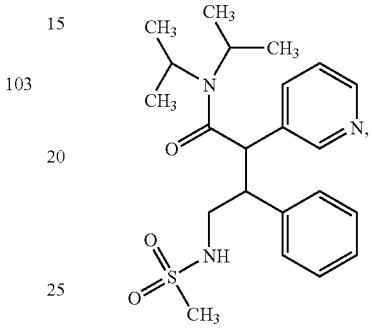
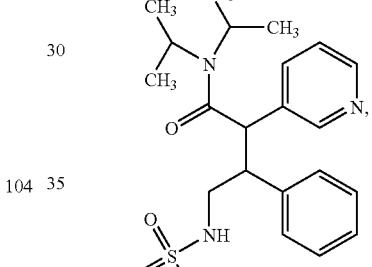
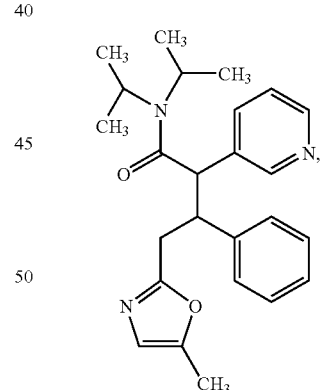
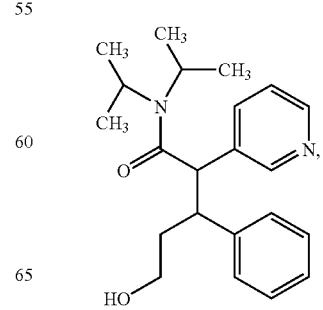

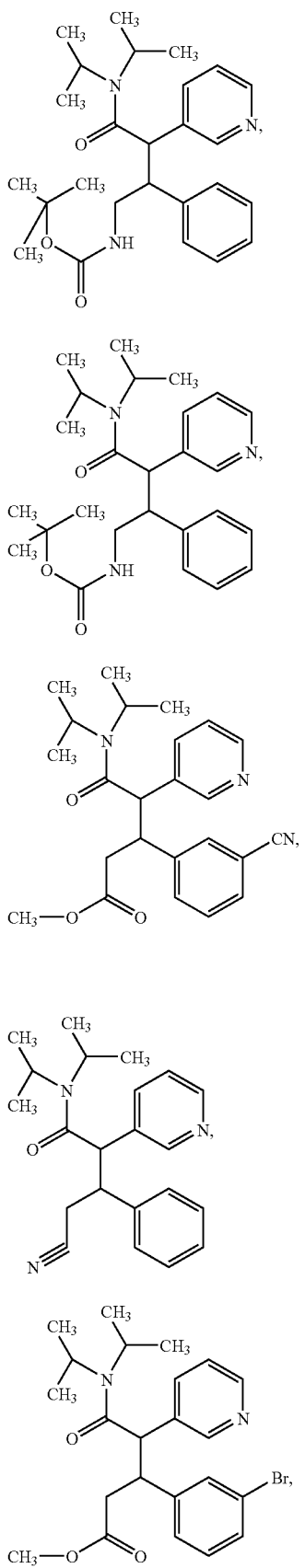
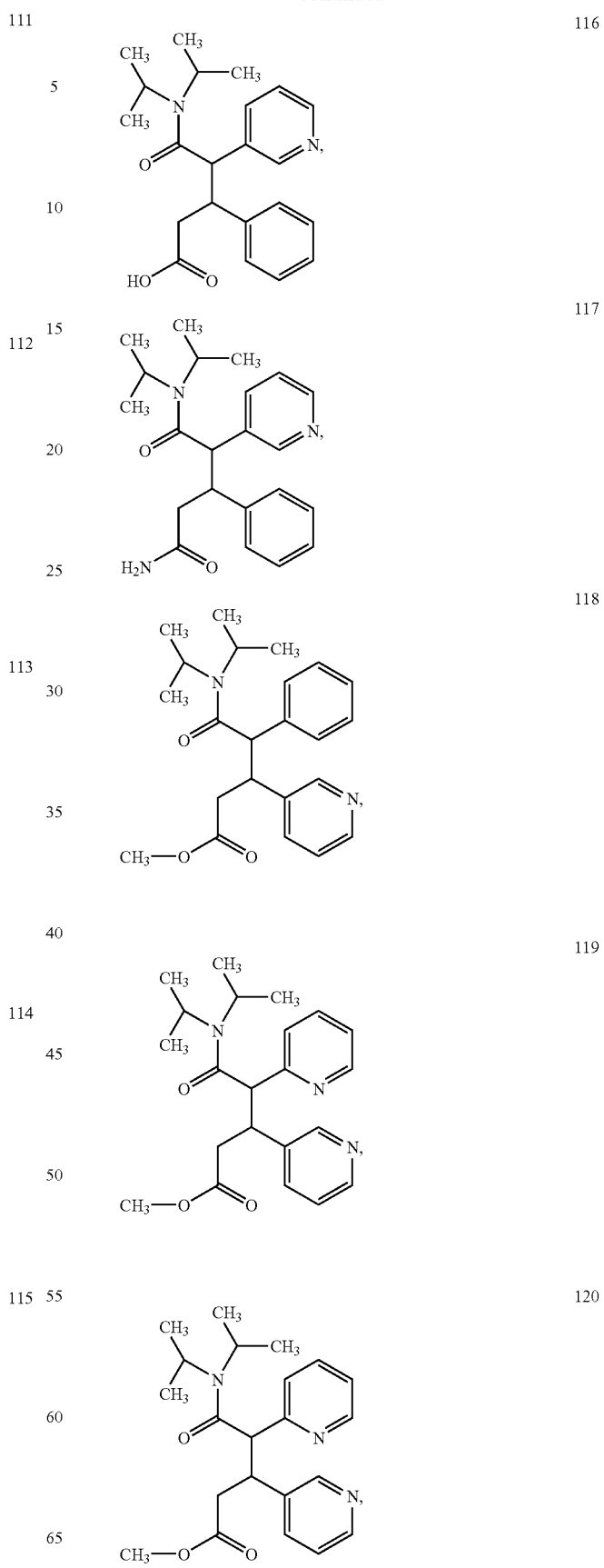

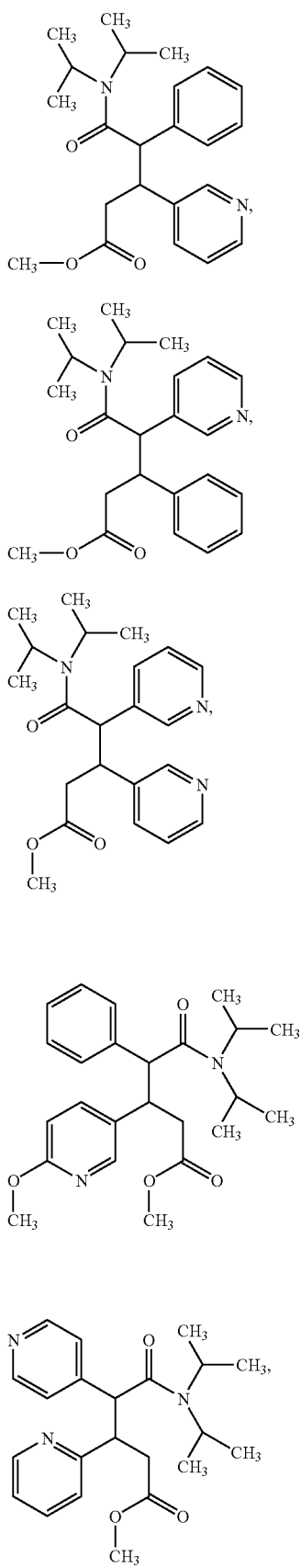
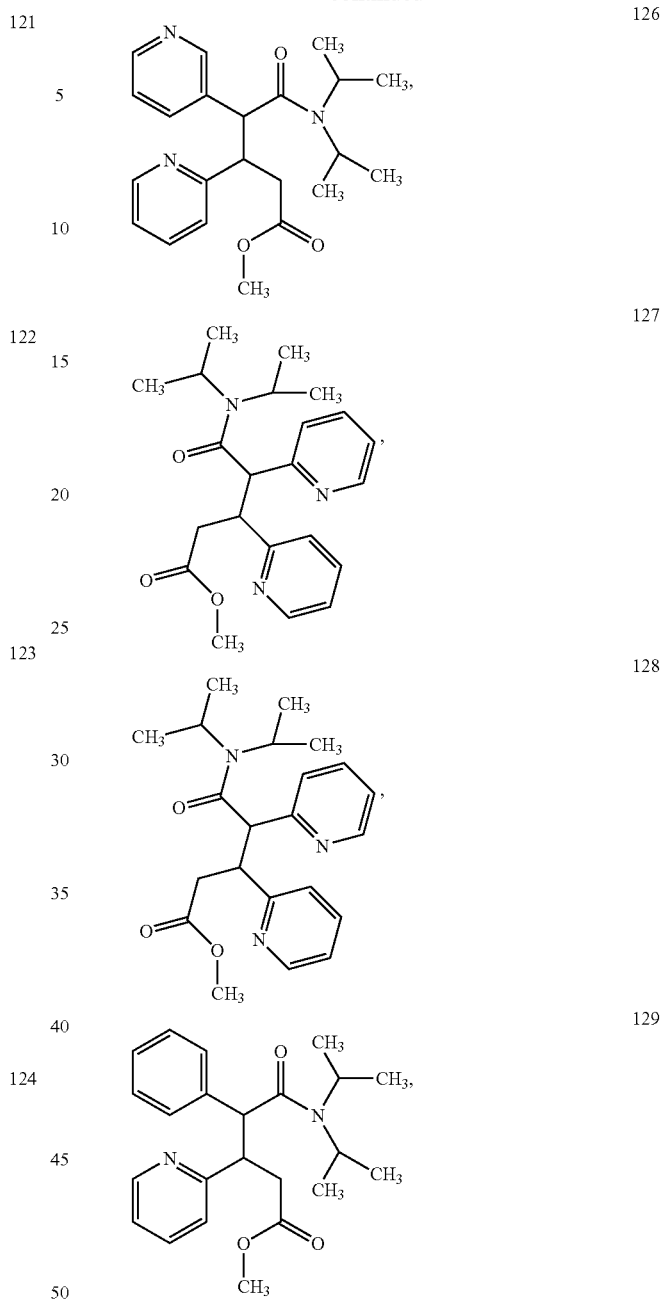

These exemplary compounds correspond to the following names:
1. N,N-diisopropyl-3-phenyl-4-[(4-phenylbutanoyl)amino]-2-pyridin-3-ylbutanamide,
2. N,N-diisopropyl-3-phenyl-4-[({[(1S)-1-phenylethyl]amino}carbonyl)amino]-2-pyridin-3-ylbutanamide,
3. N,N-diisopropyl-3-phenyl-4-[(3-phenylpropanoyl)amino]-2-pyridin-3-ylbutanamide,
4. 4-{[3-(2-fluorophenyl)propanoyl]amino}-N,N-diisopropyl-3-phenyl-2-pyridin-3-ylbutanamide,
5. N,N-diisopropyl-3-phenyl-4-[(3-phenylbutanoyl)amino]-2-pyridin-3-ylbutanamide,
6. N,N-diisopropyl-4-({[(3-methylbenzyl)amino]carbonyl}amino)-3-phenyl-2-pyridin-3-ylbutanamide,
7. 4-({[(4-bromobenzyl)amino]carbonyl}amino)-N,N-diisopropyl-3-phenyl-2-pyridin-3-ylbutanamide, 8 4-({[(4-fluorobenzyl)amino]carbonyl}amino)-N,N-diisopropyl-3-phenyl-2-pyridin-3-ylbutanamide,
9 N,N-diisopropyl-3-phenyl-4-[({[(1R,2S)-2-phenylcyclopropyl]amino}carbonyl)amino]-2-pyridin-3-ylbutanamide,
10 N,N-diisopropyl-4-[({[1-(1-naphthyl)ethyl]amino}carbonyl)amino]-3-phenyl-2-pyridin-3-ylbutanamide,
11 4-({[(3-fluorobenzyl)amino]carbonyl}amino)-N,N-diisopropyl-3-phenyl-2-pyridin-3-ylbutanamide,
12 4-[(benzylsulfonyl)amino]-N,N-diisopropyl-3-phenyl-2-pyridin-3-ylbutanamide,
13 N,N-diisopropyl-4-({[(4-methylbenzyl)amino]carbonyl}amino)-3-phenyl-2-pyridin-3-ylbutanamide,
14 4-({[(2-fluorobenzyl)amino]carbonyl}amino)-N,N-diisopropyl-3-phenyl-2-pyridin-3-ylbutanamide,
15 N,N-diisopropyl-3-phenyl-4-{[(2-phenyl-1,3-thiazol-4-yl)acetyl]amino}-2-pyridin-3-ylbutanamide,
16 4-{[3-(2-chlorophenyl)propanoyl]amino}-N,N-diisopropyl-3-phenyl-2-pyridin-3-ylbutanamide,
17 N,N-diisopropyl-4-({[(4-methoxybenzyl)amino]carbonyl}amino)-3-phenyl-2-pyridin-3-ylbutanamide,
18 N,N-diisopropyl-3-phenyl-4-({[(E)-2-phenylvinyl]sulfonyl}amino)-2-pyridin-3-ylbutanamide,
19 N,N-diisopropyl-3-phenyl-2-pyridin-3-yl-4-({[2-(trifluoromethyl)phenyl]sulfonyl}amino)butanamide,
20 N,N-diisopropyl-3-phenyl-2-pyridin-3-yl-4-[(3-pyridin-2-ylpropanoyl)amino]butanamide,
21 N,N-diisopropyl-3-phenyl-4-({[(2-phenylethyl)amino]carbonyl}amino)-2-pyridin-3-ylbutanamide,
22 4-({[(2-chlorobenzyl)amino]carbonyl}amino)-N,N-diisopropyl-3-phenyl-2-pyridin-3-ylbutanamide,
23 4-{[(cyclohexylamino)carbonyl]amino}-N,N-diisopropyl-3-phenyl-2-pyridin-3-ylbutanamide,
24 4-({[(3-fluorophenyl)amino]carbonyl}amino)-N,N-diisopropyl-3-phenyl-2-pyridin-3-ylbutanamide,
25 N,N-diisopropyl-4-{[(1-naphthylamino)carbonyl]amino}-3-phenyl-2-pyridin-3-ylbutanamide,
26 N,N-diisopropyl-3-phenyl-4-[({[(1R)-1-phenylethyl]amino}carbonyl)amino]-2-pyridin-3-ylbutanamide,
27 4-({[(diphenylmethyl)amino]carbonyl}amino)-N,N-diisopropyl-3-phenyl-2-pyridin-3-ylbutanamide,
28 N,N-diisopropyl-3-phenyl-4-[({[(1S)-1-phenylethyl]amino}carbonyl)amino]-2-pyridin-3-ylbutanamide,
29 N,N-diisopropyl-3-phenyl-4-[({[(1R)-1-phenylethyl]amino}carbonyl)amino]-2-pyridin-3-ylbutanamide,
30 N,N-diisopropyl-4-({[(4-methylbenzyl)amino]carbonyl}amino)-3-phenyl-2-pyridin-3-ylbutanamide,
31 4-({[(4-fluorobenzyl)amino]carbonyl}amino)-N,N-diisopropyl-3-phenyl-2-pyridin-3-ylbutanamide,
32 N,N-diisopropyl-3-phenyl-4-({[(2-phenylethyl)amino]carbonyl}amino)-2-pyridin-3-ylbutanamide,
33 N,N-diisopropyl-4-({[(3-methylbenzyl)amino]carbonyl}amino)-3-phenyl-2-pyridin-3-ylbutanamide,
34 4-({[(4-bromobenzyl)amino]carbonyl}amino)-N,N-diisopropyl-3-phenyl-2-pyridin-3-ylbutanamide,
35 4-({[(3-fluorobenzyl)amino]carbonyl}amino)-N,N-diisopropyl-3-phenyl-2-pyridin-3-ylbutanamide,
36 N,N-diisopropyl-4-({[(4-methoxybenzyl)amino]carbonyl}amino)-3-phenyl-2-pyridin-3-ylbutanamide,
37 4-[(benzylsulfonyl)amino]-N,N-diisopropyl-3-phenyl-2-pyridin-3-ylbutanamide,
38 N,N-diisopropyl-3-phenyl-4-({[(E)-2-phenylvinyl]sulfonyl}amino)-2-pyridin-3-ylbutanamide,
39 4-({[(2-chlorobenzyl)amino]carbonyl}amino)-N,N-diisopropyl-3-phenyl-2-pyridin-3-ylbutanamide,
40 4-({[(2-fluorobenzyl)amino]carbonyl}amino)-N,N-diisopropyl-3-phenyl-2-pyridin-3-ylbutanamide,
41 N,N-diisopropyl-4-[({[1-(1-naphthyl)ethyl]amino}carbonyl)amino]-3-phenyl-2-pyridin-3-ylbutanamide,
42 N,N-diisopropyl-3-phenyl-4-[({[(1R,2S)-2-phenylcyclopropyl]amino}carbonyl)amino]-2-pyridin-3-ylbutanamide,
43 N,N-diisopropyl-3-phenyl-2-pyridin-3-yl-4-({[2-(trifluoromethyl)phenyl]sulfonyl}amino)butanamide,
44 N,N-diisopropyl-4-{[(1-naphthylamino)carbonyl]amino}-3-phenyl-2-pyridin-3-ylbutanamide,
45 4-{[(cyclohexylamino)carbonyl]amino}-N,N-diisopropyl-3-phenyl-2-pyridin-3-ylbutanamide,
46 4-{[(sec-butylamino)carbonyl]amino}-N,N-diisopropyl-3-phenyl-2-pyridin-3-ylbutanamide,
47 4-({[(diphenylmethyl)amino]carbonyl}amino)-N,N-diisopropyl-3-phenyl-2-pyridin-3-ylbutanamide,
48 4-({[(3-fluorophenyl)amino]carbonyl}amino)-N,N-diisopropyl-3-phenyl-2-pyridin-3-ylbutanamide,
49 4-{[3-(2-fluorophenyl)propanoyl]amino}-N,N-diisopropyl-3-phenyl-2-pyridin-3-ylbutanamide,
50 N,N-diisopropyl-3-phenyl-4-[(3-phenylpropanoyl)amino]-2-pyridin-3-ylbutanamide,
51 N,N-diisopropyl-3-phenyl-4-[(3-phenylbutanoyl)amino]-2-pyridin-3-ylbutanamide,
52 N,N-diisopropyl-3-phenyl-4-[(3-phenylpropanoyl)amino]-2-pyridin-3-ylbutanamide,
53 4-{[3-(2-chlorophenyl)propanoyl]amino}-N,N-diisopropyl-3-phenyl-2-pyridin-3-ylbutanamide,
54 N,N-diisopropyl-3-phenyl-4-[(4-phenylbutanoyl)amino]-2-pyridin-3-ylbutanamide,
55 N,N-diisopropyl-3-phenyl-4-{[(2-phenyl-1,3-thiazol-4-yl)acetyl]amino}-2-pyridin-3-ylbutanamide,
56 N,N-diisopropyl-3-phenyl-2-pyridin-3-yl-4-[(3-pyridin-2-ylpropanoyl)amino]butanamide,
57 4-[(2,3-dihydro-1H-inden-2-ylacetyl)amino]-N,N-diisopropyl-3-phenyl-2-pyridin-3-ylbutanamide,
58 4-(acetylamino)-N,N-diisopropyl-3-phenyl-2-pyridin-3-ylbutanamide,
59 N,N-diisopropyl-3-phenyl-2-pyridin-3-yl-4-({[2-(trifluoromethyl)phenyl]acetyl}amino)butanamide,
60 4-{[(2-chloro-6-fluorophenyl)acetyl]amino}-N,N-diisopropyl-3-phenyl-2-pyridin-3-ylbutanamide,
61 N-[4-(diisopropylamino)-4-oxo-2-phenyl-3-pyridin-3-ylbutyl]pentanamide,
62 N,N-diisopropyl-4-{[3-(1-methyl-1H-pyrazol-4-yl)propanoyl]amino}-3-phenyl-2-pyridin-3-ylbutanamide,
63 methyl 5-{[2-(1,3-benzodioxol-5-yl)ethyl]amino}-5-oxo-3-phenyl-4-pyridin-3-ylpentanoate,
64 $N^5$-(2-fluorobenzyl)-$N^1$,$N^1$-diisopropyl-3-phenyl-2-pyridin-3-ylpentanediamide,
65 $N^1$,$N^1$-diisopropyl-3-phenyl-$N^5$-(3-phenylpropyl)-2-pyridin-3-ylpentanediamide,
66 $N^1$,$N^1$-diisopropyl-3-phenyl-$N^5$-(1-phenylethyl)-2-pyridin-3-ylpentanediamide,
67 $N^5$-[2-(tert-butylthio)ethyl]-$N^1$,$N^1$-diisopropyl-3-phenyl-2-pyridin-3-ylpentanediamide,
68 $N^1$,$N^1$-diisopropyl-3-phenyl-$N^5$-(2-phenylethyl)-2-pyridin-3-ylpentanediamide
69 $N^5$-(2,3-dihydro-1H-inden-2-yl)-$N^1$,$N^1$-diisopropyl-3-phenyl-2-pyridin-3-ylpentanediamide,
70 $N^1$,$N^1$-diisopropyl-3-phenyl-$N^5$-[(4-phenylmorpholin-2-yl)methyl]-2-pyridin-3-ylpentanediamide,
71 $N^1$,$N^1$-diisopropyl-3-phenyl-$N^5$-pyridin-2-yl-2-pyridin-3-ylpentanediamide, 72 N¹,N¹-diisopropyl-N⁵-(1-isopropyl-2-methylpropyl)-3-phenyl-2-pyridin-3-ylpentanediamide,
73 N⁵-(1H-benzimidazol-2-ylmethyl)-N¹,N¹-diisopropyl-3-phenyl-2-pyridin-3-ylpentanediamide,
74 N⁵-(3-isopropoxypropyl)-N¹,N¹-diisopropyl-3-phenyl-2-pyridin-3-ylpentanediamide,
75 N¹,N¹-diisopropyl-3-phenyl-2-pyridin-3-yl-N⁵-(pyridin-2-ylmethyl)pentanediamide,
76 methyl 5-{[5-(diisopropylamino)-5-oxo-3-phenyl-4-pyridin-3-ylpentanoyl]amino}pentanoate,
77 1-tert-butyl 5-methyl 3-phenyl-2-pyridin-3-ylpentanedioate,
78 methyl 4-(3-cyanophenyl)-5-(diisopropylamino)-5-oxo-3-pyridin-3-ylpentanoate,
79 1-tert-butyl 5-methyl 3-phenyl-2-pyridin-3-ylpentanedioate,
80 methyl 4-(3-bromophenyl)-5-(diisopropylamino)-5-oxo-3-pyridin-3-ylpentanoate,
81 N¹,N¹-diisopropyl-N⁵,N⁵-dimethyl-3-phenyl-2-pyridin-3-ylpentanediamide,
82 N¹,N¹-diisopropyl-N⁵-methyl-3-phenyl-2-pyridin-3-ylpentanediamide,
83 methyl 5-(diisopropylamino)-5-oxo-4-pyridin-3-yl-3-pyridin-4-ylpentanoate,
84 5-methoxy-5-oxo-3-phenyl-2-pyridin-3-ylpentanoic acid,
85 methyl 5-(diisopropylamino)-5-oxo-4-pyridin-3-yl-3-pyridin-4-ylpentanoate,
86 methyl 5-(diisopropylamino)-5-oxo-3-phenyl-4-pyridin-2-ylpentanoate,
87 methyl 5-(diisopropylamino)-5-oxo-4-pyridin-2-yl-3-pyridin-4-ylpentanoate,
88 methyl 5-(diisopropylamino)-5-oxo-3,4-dipyridin-4-ylpentanoate,
89 methyl 5-(diisopropylamino)-5-oxo-4-phenyl-3-pyridin-4-ylpentanoate,
90 methyl 5-(diisopropylamino)-5-oxo-3-phenyl-4-pyridin-4-ylpentanoate,
91 methyl 5-(diisopropylamino)-5-oxo-3,4-diphenylpentanoate,
92 methyl 5-(diisopropylamino)-5-oxo-3,4-diphenylpentanoate,
93 3-(3-cyanophenyl)-4-({[(2-fluorobenzyl)amino]carbonyl}amino)-N,N-diisopropyl-2-pyridin-3-ylbutanamide,
94 3-(3-cyanophenyl)-4-({[(2-fluorobenzyl)amino]carbonyl}amino)-N,N-diisopropyl-2-pyridin-3-ylbutanamide,
95 3-(3-cyanophenyl)-4-({[(2-fluorobenzyl)amino]carbonyl}amino)-N,N-diisopropyl-2-pyridin-3-ylbutanamide,
96 N-[4-(diisopropylamino)-4-oxo-2-phenyl-3-pyridin-3-ylbutyl]-2-fluoro-N-(methylsulfonyl)phenylalaninamide,
97 N-[4-(diisopropylamino)-4-oxo-2-phenyl-3-pyridin-3-ylbutyl]-2-fluorophenylalaninamide,
98 N-(tert-butoxycarbonyl)-N-[4-(diisopropylamino)-4-oxo-2-phenyl-3-pyridin-3-ylbutyl]-2-fluorophenylalaninamide,
99 N,N-diisopropyl-4-(5-methyl-1,2,4-oxadiazol-3-yl)-3-phenyl-2-pyridin-3-ylbutanamide,
100 N,N-diisopropyl-4-(2-methyl-2H-tetrazol-5-yl)-3-phenyl-2-pyridin-3-ylbutanamide
101 N,N-diisopropyl-4-(1-methyl-1H-tetrazol-5-yl)-3-phenyl-2-pyridin-3-ylbutanamide,
102 5-hydrazino-N,N-diisopropyl-5-oxo-3-phenyl-2-pyridin-3-ylpentanamide,
103 N,N-diisopropyl-4-(3-methyl-1,2,4-oxadiazol-5-yl)-3-phenyl-2-pyridin-3-ylbutanamide,
104 N,N-diisopropyl-4-(3-methyl-1,2,4-oxadiazol-5-yl)-3-phenyl-2-pyridin-3-ylbutanamide,
105 N,N-diisopropyl-4-(5-methyl-1,3-oxazol-2-yl)-3-phenyl-2-pyridin-3-ylbutanamide,
106 4-cyano-N,N-diisopropyl-3-phenyl-2-pyridin-3-ylbutanamide,
107 N,N-diisopropyl-4-[(methylsulfonyl)amino]-3-phenyl-2-pyridin-3-ylbutanamide,
108 N,N-diisopropyl-4-[(methylsulfonyl)amino]-3-phenyl-2-pyridin-3-ylbutanamide,
109 N,N-diisopropyl-4-(5-methyl-1,3-oxazol-2-yl)-3-phenyl-2-pyridin-3-ylbutanamide,
110 5-hydroxy-N,N-diisopropyl-3-phenyl-2-pyridin-3-ylpentanamide,
111 tert-butyl 4-(diisopropylamino)-4-oxo-2-phenyl-3-pyridin-3-ylbutylcarbamate,
112 tert-butyl 4-(diisopropylamino)-4-oxo-2-phenyl-3-pyridin-3-ylbutylcarbamate,
113 methyl 3-(3-cyanophenyl)-5-(diisopropylamino)-5-oxo-4-pyridin-3-ylpentanoate,
114 4-cyano-N,N-diisopropyl-3-phenyl-2-pyridin-3-ylbutanamide,
115 methyl 3-(3-bromophenyl)-5-(diisopropylamino)-5-oxo-4-pyridin-3-ylpentanoate,
116 5-(diisopropylamino)-5-oxo-3-phenyl-4-pyridin-3-ylpentanoic acid,
117 N¹,N¹-diisopropyl-3-phenyl-2-pyridin-3-ylpentanediamide,
118 methyl 5-(diisopropylamino)-5-oxo-4-phenyl-3-pyridin-3-ylpentanoate,
119 methyl 5-(diisopropylamino)-5-oxo-4-pyridin-2-yl-3-pyridin-3-ylpentanoate,
120 methyl 5-(diisopropylamino)-5-oxo-4-pyridin-2-yl-3-pyridin-3-ylpentanoate,
121 methyl 5-(diisopropylamino)-5-oxo-4-phenyl-3-pyridin-3-ylpentanoate,
122 methyl 5-(diisopropylamino)-5-oxo-3-phenyl-4-pyridin-3-ylpentanoate,
123 methyl 5-(diisopropylamino)-5-oxo-3,4-dipyridin-3-ylpentanoate,
124 methyl 5-(diisopropylamino)-3-(6-methoxypyridin-3-yl)-5-oxo-4-phenylpentanoate,
125 methyl 5-(diisopropylamino)-5-oxo-3-pyridin-2-yl-4-pyridin-4-ylpentanoate,
126 methyl 5-(diisopropylamino)-5-oxo-4-pyridin-2-yl-3-pyridin-3-ylpentanoate,
127 methyl 5-(diisopropylamino)-5-oxo-3,4-dipyridin-2-ylpentanoate,
128 methyl 5-(diisopropylamino)-5-oxo-3,4-dipyridin-2-ylpentanoate, and
129 methyl 5-(diisopropylamino)-5-oxo-4-phenyl-3-pyridin-2-ylpentanoate.

Another embodiment of the invention is a compound wherein X is —OR².

Preferred compounds of this embodiment include those wherein
R² is hydrogen or C₁₋₆ alkyl;
Z is —C(O)OC₁₋₆ alkyl;
Ar³ is a heteroaryl ring, wherein the point of attachment to the heteroaryl ring is a carbon atom, and the heteroaryl ring is a 6-membered unsaturated monocyclic ring with 1, 2, 3, or 4 heteroatom ring atoms selected from the group consisting of N, O or S, wherein said heteroaryl ring is unsubstituted, mono-substituted with R⁴, disubstituted with groups independently selected from R⁴, trisubstituted with groups independently selected from R⁴, or tetrasubstituted with groups independently selected from R⁴, and wherein any stable S or N heteroaryl ring atom is unsubstituted or substituted with oxo, said heteroaryl ring $R^4$ substitutions being on one or more heteroaryl ring carbon atoms; and $Ar^4$ is an aryl ring, wherein the aryl ring is unsubstituted, mono-substituted with $R^4$, disubstituted with groups independently selected from $R^4$, trisubstituted with groups independently selected from $R^4$, or tetrasubstituted with groups independently selected from $R^4$.

An example of a compound of this preferred embodiment is a compound selected from the group consisting of

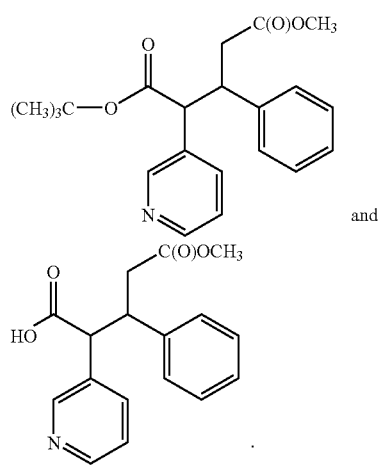

and

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppressant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an anti-tachycardia device (e.g. a defibrillator or a pacemaker) in combination with a compound of Claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —$CH_2C(O)$— groups (keto forms) may undergo tautomerism to form hydroxyl —$CH=C(OH)$— groups (enol forms). Both keto and enol forms are included within the scope of the present invention.

In addition compounds with carbon-carbon double bonds may occur in Z- and E-forms with all isomeric forms of the compounds being included in the present invention.

LIST OF ABBREVIATIONS

AAS atomic absorption spectroscopy
AIDS acquired immunodeficiency syndrome
AF atrial fibrillation
ACE angiotensin converting enzyme
APD action potential duration
$CH_2Cl_2$ dichloromethane
CHO Chinese hamster ovary
DCM dichloromethane
DIPEA N,N,N-diisopropylethylamine
DMF dimethylformamide
DMSO dimethylsulfoxide
DPPA diphenylphosphoryl azide
EDC 1-ethyl-3-(3-dimethylaminopropyl) carbodiimide hydrochloride
EDTA ethylenediaminetetraacetic acid
$Et_3N$ triethylamine
EtOH ethanol
FAAS flame atomic absorption spectroscopy
FBS fetal bovine serum
HBSS Hank's balanced salt solution
HCl hydrochloric acid
HEPES N-2-hydroxyethylpiperazine-N'-2-ethanesulphonic acid
HOAt 1-hydroxy-7-azabenzotriazole
HPLC high pressure liquid chromatography
HRMS high resolution mass spectrum
INH inhibition
KCl potassium chloride
$K_3PO_4$ potassium phosphate tribasic
LDA lithium diisopropylamide
LYS lysate
MeOH methanol
$MgCl_2$ magnesium chloride
MS mass spectrum NaCl sodium chloride
NaH sodium hydride
NaHCO$_3$ sodium bicarbonate
NaN$_3$ sodium azide
NaOH sodium hydroxide
Na$_2$SO$_4$ sodium sulfate
Na$_2$S$_2$O$_3$ sodium thiosulfate
Na$_3$PO$_4$ sodium phosphate tribasic
n-BuLi n-butyllithium
t-Bu-OH tert-butyl alcohol
NH$_4$Cl ammonium chloride
NH$_4$OH ammonium hydroxide
NMR nuclear magnetic resonance
NSAID non-steroidal antiinflammatory drug
PBS phosphate-buffered saline
POCl$_3$ phosphorus oxychloride
SOCl$_2$ thionyl chloride
SUP supernatant
TAFI thrombin-activatable fibrinolysis inhibitor
TFA trifluoroacetic acid
THF tetrahydrofuran
TMS tetramethylsilane (molecule) or trimethylsilyl (substituent)

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes all of the hexyl alkyl and pentyl alkyl isomers as well as n-, iso-, sec- and t-butyl, n- and isopropyl, ethyl and methyl. "C$_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-C$_4$alkylene-B" represents A—CH$_2$—CH$_2$—CH$_2$—CH$_2$—B. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "CH$_2$CH$_2$" or alternatively, by "H$_2$C=CH$_2$". "C$_{2-5}$ alkenyl" (or "C$_2$-C$_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "C$_{2-3}$ alkenyl" have an analogous meaning.

The term "alkynyl" includes both branched and straight chain unsaturated hydrocarbon groups containing at least two carbon atoms joined by a triple bond. The alkyne acetyylene is represented, for example, by "CHCH" or alternatively, by "HC≡CH". "C$_{2-5}$ alkynyl" (or "C$_2$-C$_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "C$_{2-3}$ alkynyl" have an analogous meaning.

Unless otherwise specifically noted as only "unsubstituted" or only "substituted", alkyl, alkylene, alkoxy, alkenyl and alkynyl groups are unsubstituted or substituted with 1 to 3 substituents on each carbon atom, with halo, C$_1$-C$_{20}$ alkyl, CF$_3$, NH$_2$, N(C$_1$-C$_6$ alkyl)$_2$, NO$_2$, oxo, CN, N3, —OH, —O(C$_1$-C$_6$ alkyl), C$_3$-C$_{10}$ cycloalkyl, C$_2$-C$_6$ alkenyl, C$_2$-C$_6$ alkynyl, (C$_0$-C$_6$ alkyl) S(O)$_{0-2}$—, (C$_0$-C$_6$ alkyl)S(O)$_{0-2}$(C$_0$-C$_6$ alkyl)-, (C$_0$-C$_6$ alkyl)C(O)NH—, H$_2$N—C(NH)—, —O(C$_1$-C$_6$ alkyl)CF$_3$, (C$_0$-C$_6$ alkyl)C(O)—, (C$_0$-C$_6$ alkyl)OC(O)—, (C$_0$-C$_6$ alkyl)O(C$_1$-C$_6$ alkyl)-, (C$_0$-C$_6$ alkyl)C(O)$_{1-2}$(C$_0$-C$_6$ alkyl)-, (C$_0$-C$_6$ alkyl)OC(O)NH—, —NH(C$_1$-C$_6$ alkyl)NHC(O)NH(C$_1$-C$_6$ alkyl), NHC(O)OC$_1$-C$_6$ alkyl, —NH(C$_1$-C$_6$ alkyl)NHSO$_2$(C$_1$-C$_6$ alkyl), —(C$_0$-C$_6$ alkyl)NHSO$_2$(C$_1$-C$_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "C$_0$" as employed in expressions such as "C$_{0-6}$ alkyl" means a direct covalent bond. Similarly, when an integer defining the presence of a certain number of atoms in a group is equal to zero, it means that the atoms adjacent thereto are connected directly by a bond. For example, in the structure

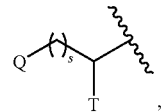

wherein s is an integer equal to zero, 1 or 2, the structure is

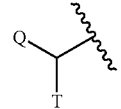

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "C$_{1-6}$ haloalkyl" (which may alternatively be referred to as "C$_1$-C$_6$ haloalkyl" or "halogenated C$_1$-C$_6$ alkyl") means a C$_1$ to C$_6$ linear or branched alkyl group as defined above with one or more halogen substituents. The term "C$_{1-4}$ haloalkyl" has an analogous meaning. The term "C$_{1-6}$ fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

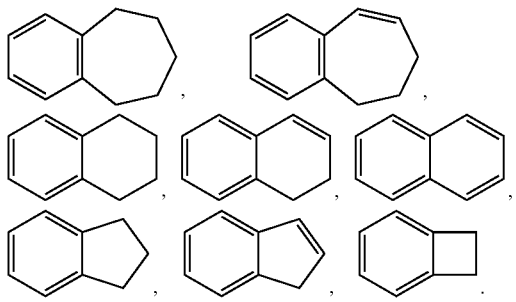

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(N)—, —O($C_1$-$C_6$ alkyl) $CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the terra "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyridinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 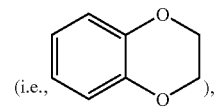), imidazo(2,1-b)(1,3)thiazole, (i.e., 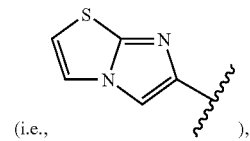), and benzo-1,3-dioxolyl (i.e., 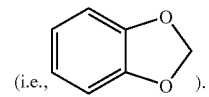).

In certain contexts herein,

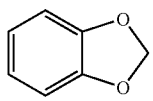

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . .") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

which have equivalent meanings.

Structural representations of compounds having substituents terminating with a methyl group may display the terminal methyl group either using the characters "$CH_3$", e.g. "—$CH_3$" or using a straight line representing the presence of the methyl group, e.g.

i.e.,

and

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

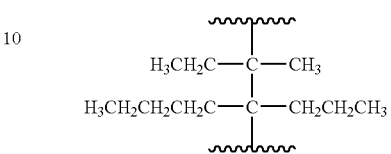

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto.

SCHEME I

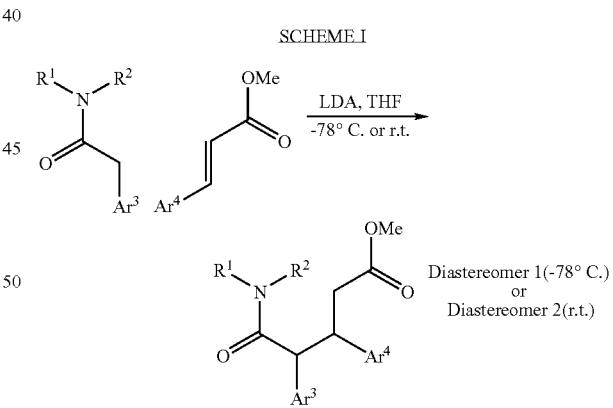

$R^1$, $R^2$, $Ar^3$, and $Ar^4$ are as previously defined.

Example I-1

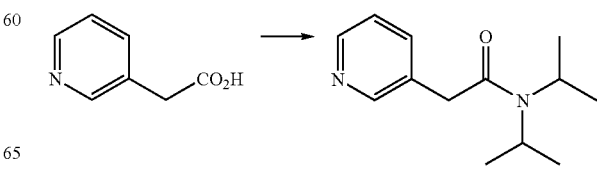

N,N-diisopropyl-2-pyridin-3-ylacetamide

To a mixture of pyridin-3-ylacetic acid (1.0 g, 7.292 mmol), EDC (2.796 g, 14.584 mmol) and HOAt (992 mg, 7.292 mmol) in 10 mL DMF were added diisopropyl amine (1.476 g, 14.584 mmol) and Hunig's base (1.885 g, 14.584 mmol). The reaction mixture was stirred at room temperature overnight and then partitioned between ether and half-saturated aq $NaHCO_3$. The aqueous layer was extracted with $CH_2Cl_2$ (3×). The combined organic layers were dried over anhydrous $Na_2SO_4$ and concentrated. The resulting residue was purified by flash chromatography using a linear gradient of 0% to 6% MeOH—$NH_3$ (90:10 v/v) in $CH_2Cl_2$ to give a white solid.

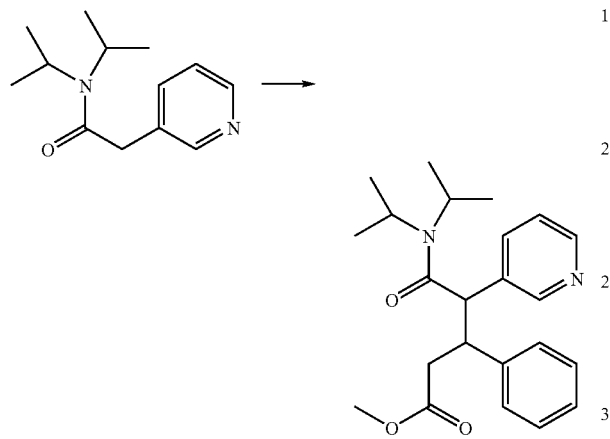

methyl 5-(diisopropylamino)-5-oxo-3-phenyl-4-pyridin-3-ylpentanoate (Diastereomer 1)

To a cold (0° C.) solution of N,N-diisopropyl-2-pyridin-3-ylacetamide (200 mg, 0.908 mmol) in dry THF (8 mL) was added a solution of LDA (2 M) in THF (0.908 mL, 1.816 mmol). The reaction mixture was stirred at 0° C. for 30 min and then cooled to −78° C. Solid methyl cinnamate (177 mg, 1.09 mmol) was added in one portion and stirred at −78° C. After 2 h the reaction was quenched by adding a saturated aqueous solution of $NH_4Cl$, warmed up to rt and then partitioned between $CH_2Cl_2$ and saturated aqueous $NaHCO_3$. The aqueous layer was extracted with $CH_2Cl_2$ (3×). The combined organic layers were dried over anhydrous $Na_2SO_4$ and concentrated. The resulting red viscous liquid was purified by r.p. HPLC. The desired fractions were combined and the product was isolated as a free base by extraction from saturated aqueous $NaHCO_3$. Mixture of diastereomers (91:9).

$^1$H NMR (major diastereomer, 500 MHz, $CDCl_3$): δ 8.58 (d, J=1.7 Hz, 1H), 8.55-8.54 (m, 1H), 8.03 (d, J=7.8 Hz, 1H), 7.34-7.25 (m, 5H), 7.21-7.18 (m, 1H), 4.15-3.99 (m, 3H), 3.39 (s, 3H), 3.12-3.06 (m, 1H), 2.48-2.38 (m, 2H), 1.17 (d, J=6.6 Hz, 3H), 0.93 (d, J=6.8 Hz, 3H), 0.88 (d, J=6.6 Hz, 3H), 0.85 (d, J=6.6 Hz, 3H). HRMS: observed, 383.2318; calculated, 383.2329

Example I-2

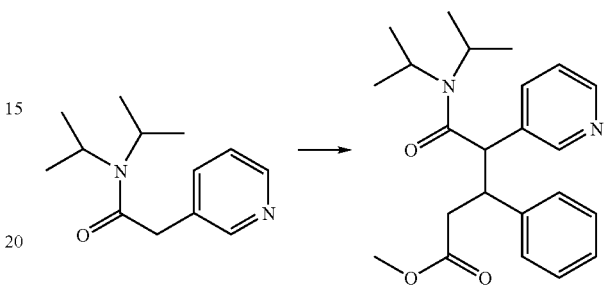

methyl 5-(diisopropylamino)-5-oxo-3-phenyl-4-pyridin-3-ylpentanoate (Diastereomer 2)

To a cold (0° C.) solution of N,N-diisopropyl-2-pyridin-3-ylacetamide (740 mg, 3.36 mmol) in dry THF (30 mL) was added a solution of LDA (1.5 M) in THF (4.5 mL, 6.72 mmol). The reaction mixture was stirred at 0° C. for 30 min and then cooled to −78° C. Solid methyl cinnamate (654 mg, 4.031 mmol) was added in one portion. The cooling bath was removed and the reaction mixture was allowed to warm up to room temperature. After 1.5 h, the reaction was quenched by adding a saturated aqueous solution of $NH_4Cl$ and partitioned between $CH_2Cl_2$ and saturated aqueous $NaHCO_3$. The aqueous layer was extracted with $CH_2Cl_2$ (3×). The combined organic layers were dried over anhydrous $Na_2SO_4$ and concentrated. The resulting red viscous liquid was purified by flash chromatography using a linear gradient of 0% to 5% MeOH—$NH_3$ (90:10 v/v) in $CH_2Cl_2$. Yellow solid, single diastereomer.

$^1$H NMR (500 MHz, $CDCl_3$): δ 8.30-8.29 (m, 1H), 8.08 (d, J=2.2 Hz, 1H), 7.58 (d, J=7.8 Hz, 1H), 7.11-7.04 (m, 4H), 6.98-6.96 (m, 2H), 4.11-4.06 (m, 1H), 4.00 (d, J=10.7 Hz, 1H), 3.91-3.86 (m, 1H), 3.51 (s, 3H), 3.36 br, 1H), 3.00 (dd, J=15.4, 3.9 Hz, 1H), 2.80 (dd, J=15.4, 9.8 Hz, 1H), 1.46 (d, J=6.6 Hz, 31H), 1.33 (d, J=6.8 Hz, 3H), 1.23 (d, J=6.6 Hz, 3H), 0.72 (d, J=6.1 Hz, 3H).

SCHEME II

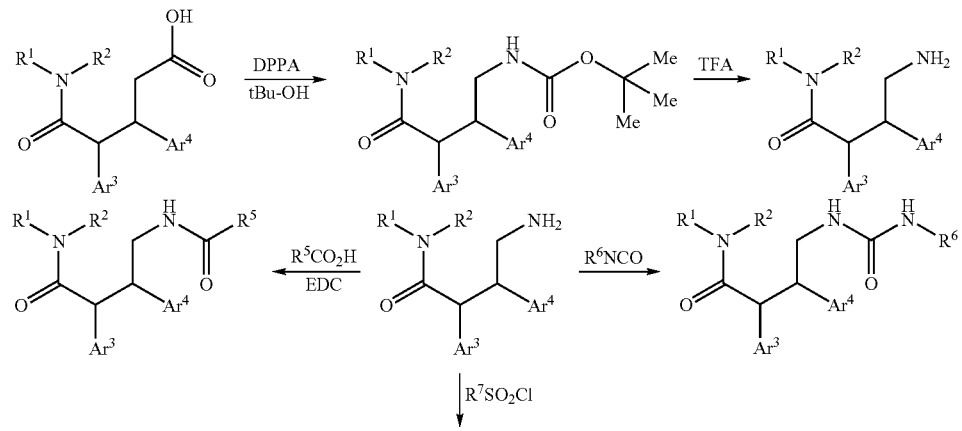

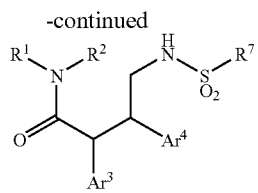

wherein $R^5$ is —$C_{1-6}$alkylene-A, —O—$C_{1-6}$alkyl or —$C_{1-6}$alkyl, $R^6$ is —$C_{0-6}$alkylyene-A, $C_{1-6}$alkyl, or

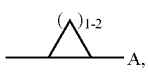

$R^7$ is —$C_{0-6}$alkylene-A, —$C_{1-6}$alkenyl-A, or $C_{1-6}$alkyl, and $R^1$, $R^2$, $Ar^3$, $Ar^4$, and A are as previously defined.

Example II-1

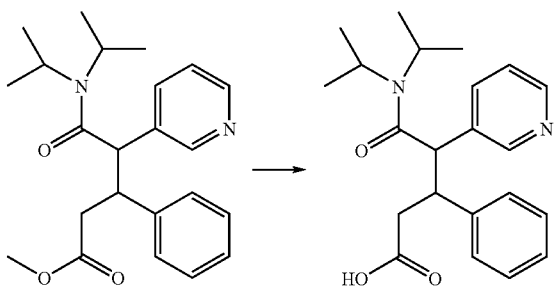

5-(diisopropylamino)-5-oxo-3-phenyl-4-pyridin-3-ylpentanoic acid

To a solution of methyl 5-(diisopropylamino)-5-oxo-3-phenyl-4-pyridin-3-ylpentanoate (Diastereomer 2, 1.095 g, 2.863 mmol) in EtOH (13 mL) was added water (15 mL) followed by 1 N aqueous NaOH (5.725 mL). The reaction mixture was stirred at room temperature. After 24 h, 1N HCl (5.725 mL) was added. The mixture was then extracted with $CH_2Cl_2$ (4×). The combined organic layers were dried over anhydrous $Na_2SO_4$ and concentrated to give a light yellow solid.

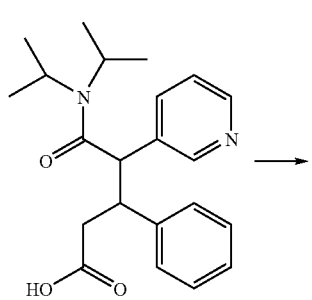

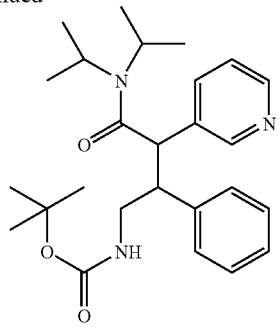

tert-butyl [4-(diisopropylamino)-4-oxo-2-phenyl-3-pyridin-3-ylbutyl]carbamate

A suspension of 5-(diisopropylamino)-5-oxo-3-phenyl-4-pyridin-3-ylpentanoic acid (5.87 g, 15.93 mmol) and powdered molecular sieves (4 A) in t-BuOH (200 mL) was stirred at room temperature for 10 min under argon. To this mixture was then added DPPA (4.12 mL, 19.1 mmol) followed by $Et_3N$ (2.66 mL, 19.1 mmol), and the reaction mixture was heated at reflux temperature. After 25 h, it was cooled down to rt, filtered through a pad of celite (washing with $CH_2Cl_2$). The combined filtrate and washings were concentrated. The residue was partitioned between $CH_2Cl_2$ and saturated aqueous $NaHCO_3$. The aqueous layer was extracted with $CH_2Cl_2$ (3×). The combined organic layers were dried over anhydrous $Na_2SO_4$ and concentrated. Purification by flash chromatography using a linear gradient of 0% to 5% MeOH—$NH_4OH$ (90:10 v/v) in $CH_2Cl_2$ gave a pale yellow solid.

$^1$H NMR (500 MHz, $CDCl_3$): δ 8.27 (d, J=3.7 Hz, 1H), 8.10 (d, J=1.7 Hz, 1H), 7.52 (br, 1H), 7.12-7.03 (m, 4H), 6.96 (d, J=7.3 Hz, 2H), 4.59 (br, 1H), 4.14-4.02 (m, 1H), 3.88 (d, J=10.3 Hz, 1H), 3.76-3.63 (m, 2H), 3.56-3.48 (m, 1H), 3.36 (br, 1H), 1.51 (d, J=6.8 Hz, 3H), 1.36 (s, 9H), 1.32 (d, J=6.8 Hz, 3H), 1.24 (d, J=6.6 Hz, 3H), 0.72 (br, 3H). HRMS: observed, 440.2912; calculated, 440.2908.

Example II-2

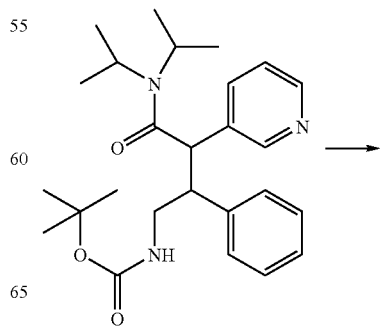

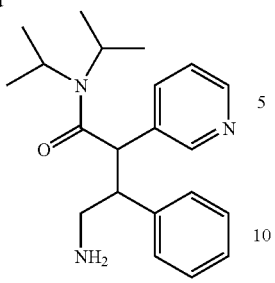

4-amino-N,N-diisopropyl-3-phenyl-2-pen
din-3-ylbutanamide

To a cold (0° C.) solution of tert-butyl [4-(diisopropylamino)-4-oxo-2-phenyl-3-pyridin-3-ylbutyl]carbamate (5.72 g, 13.01 mmol) in 20 mL of CH₂Cl₂ was added TFA (10 mL). The cooling bath was removed and the reaction mixture was stirred at room temperature for 3 h, then concentrated. The residue was partitioned between CH₂Cl₂ and saturated aqueous NaHCO₃. The aqueous layer was extracted with CH₂Cl₂ (3×). The combined organic layers were dried over anhydrous Na₂SO₄ and concentrated. Purification by flash chromatography using a linear gradient of 1% to 12% MeOH—NH₄OH (90:10 v/v) in CH₂Cl₂ gave a white solid. Single diastereomer.

¹H NMR (500 MHz, CDCl₃): δ 8.27-8.26 (m, 1H), 8.11 (d, J=1.9 Hz, 1H), 7.59 (d, J=8.1 Hz, 1H), 7.15-7.12 (m, 2H), 7.08-7.04 (m, 2H), 6.98 (d, J=7.3 Hz, 2H), 4.19-4.15 (m, 1H), 3.89 (d, J=10.5 Hz, 1H), 3.54-3.49 (m, 1H), 3.38 (br, 1H), 3.24-3.22 (m, 1H), 2.94-2.89 (m, 1H), 1.48 (d, J=6.6 Hz, 3H), 1.32 (d, J=6.6 Hz, 3H), 1.26 (d, J=6.6 Hz, 3H), 0.82 (d, J=5.9 Hz, 3H).

Example II-3

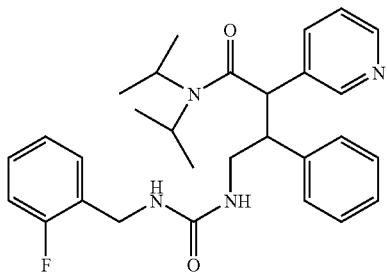

1-(3-(diisopropylcarbamoyl)-2-phenyl-3-(pyridin-3-yl)propyl)-3-(2-fluorobenzyl)-urea To a solution of 4-amino-N,N-diisopropyl-3-phenyl-2-(pyridin-3-yl)butanamide (0.030 g, 0.09 mmol) in dry DCM (2 mL) was added 1-fluoro-2-(isocyanatomethyl)benzene (0.028 g, 0.18 mmol), and DIPEA (0.023 mL, 0.135 mmol). The reaction mixture was agitated for 15 h at room temperature before adding PS-trisamine (0.022 g, 0.09 mmol) and agitating for 1 h at room temperature. The crude product was then filtered to remove the solid phase and concentrated. Purification of enantiomers by ChiralPak AD (n-hexanes/ EtOH, 85:15) yielded (−)-1-(3-(diisopropylcarbamoyl)-2-phenyl-3-(pyridin-3-yl)propyl)-3-(2-fluorobenzyl)urea as a foamy, off-white solid. Analytical LCMS: single peak (214 nm), 2.523 min. ¹H NMR (CDCl₃, 300 MHz) δ 8.26 (d, J=4.5 Hz, 1H), 8.03 (s, 1H), 7.38-7.42 (m, 2H), 7.19-7.25 (m, 1H), 6.99-7.13 (m, 6H), 6.91-6.93 (m, 2H), 4.54-4.59 (m, 1.37 (d, J=6.9 Hz, 3H), 1.26 (d, J=6.9 Hz, 3H), 1.19 (d, J=6.9 Hz, 3H), 0.60 (d, J=6.3 Hz, 3H); HRMS m/z 491.2841 (C₂₉H₃₅FN₄O₂+H requires 491.2817).

Example II-4

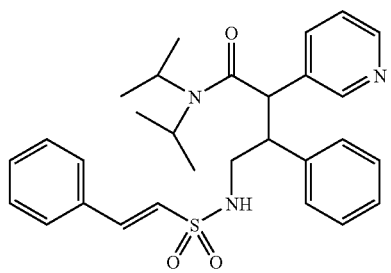

N,N-diisopropyl-3-phenyl-4-({[(E)-2-phenylvinyl]
sulfonyl}amino)-2-pyridin-3-ylbutanamide To a solution of 4-amino-N,N-diisopropyl-3-phenyl-2-(pyridin-3-yl)butanamide (0.020 g, 0.06 mmol) in dry DCM (4 mL) was added (E)-2-phenylethenesulfonyl chloride (0.025 g, 0.12 mmol), and DIPEA (0.020 mL, 0.12 mmol). The contents were agitated for 6 h at room temperature, then PS-trisamine (0.020 mg, 0.060 mmol) was added and the reaction mixture was agitated for 1 h at room temperature. Filtration of the crude product followed by reverse phase chromatography yielded N,N-diisopropyl-3-phenyl-4-({ [(E)-2-phenylvinyl]sulfonyl}amino)-2-pyridin-3-ylbutanamide as the TFA salt. Analytical LCMS: single peak (214 nm), 2.666 min. ¹H NMR (CDCl₃, 300 MHz) δ11.69 (bs, 1H), 8.46-8.49 (m, 2H), 8.22 (d, J=9 Hz, 1H), 7.54-7.58 (m, 1H), 7.38-7.43 (m, 6H), 7.07-7.14 (m, 3H), 6.98 (d, J=6 Hz, 2H), 6.56 (d, J=15 Hz, 1H), 5.12 (bs, 1H), 4.37 (d, J=9 Hz, 1H)), 4.14-4.23 (m, 1H), 3.91-4.01 (m, 1H), 3.79-3.85 (m, 1H), 1.94-2.11 (m, 1H), 1.80-1.93 (m, 1H), 1.47 (d, J=6 Hz, 3H), 1.31 (d, J=6 Hz, 3H), 1.28 (d, J=6 Hz, 3H), 0.85 (d, J=9 Hz, 3H); HRMS m/z 506.2449 (C₂₉H₃₅N₃O₃S+H⁺ requires 506.2472).

Example II-4

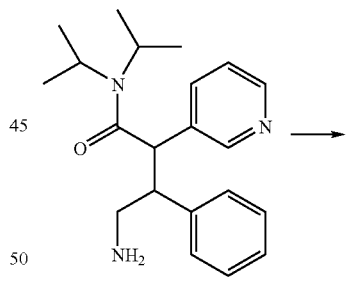

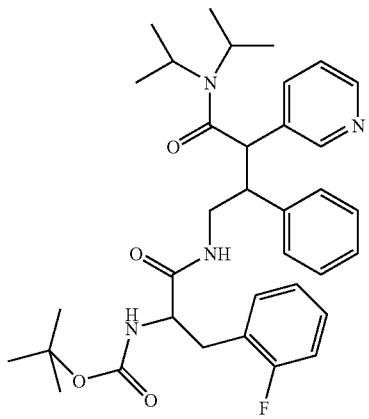

N-(tert-butoxycarbonyl)-N-[4-(diisopropylamino)-4-oxo-2-phenyl-3-pyridin-3-ylbutyl]-2-fluorophenylalaninamide To a mixture of N-(tert-butoxycarbonyl)-2-fluorophenylalanine (200 mg, 0.589 mmol), 4-amino-N,N-diisopropyl-3-phenyl-2-(pyridin-3-yl)butanamide (250 mg, 0.884 mmol), EDC (226 mg, 1.178 mmol) and HOAt (120 mg, 0.884 mmol) was added DMF (2 mL) followed by Hunig's base (0.204 mL, 1.178 mmol). The reaction mixture was stirred at room temperature overnight, then purified directly by r.p. HPLC. The desired fractions from HPLC were combined and the product was isolated as free base by extraction from aqueous NaHCO$_3$. White solid, mixture of diastereomers (1:1).

$^1$H NMR (500 MHz, CDCl$_3$): δ 8.29-8.27 (m, 1H), 8.11-8.09 (m, 1H), 7.52-7.47 (m, 1H), 7.22-7.17 (m, 1H), 7.10-6.97 (m, 7H), 6.91-6.86 (m, 2H), 6.11-6.03 (m, 1H), 4.97 (br, 1H), 4.76 (br, 1H), 4.19 (br, 2H), 4.08-4.02 (m, 2H), 3.91-3.73 (m, 4H), 3.64-3.54 (m, 4H), 3.35 (br, 2H), 3.05-2.96 (m, 2H), 2.86-2.72 (br, 2H), 1.50 (d, J=6.4 Hz, 6H), 1.35-1.23 (m, 30H), 0.69-0.65 (m, 6H). HRMS: observed, 605.3459; calculated, 605.3498.

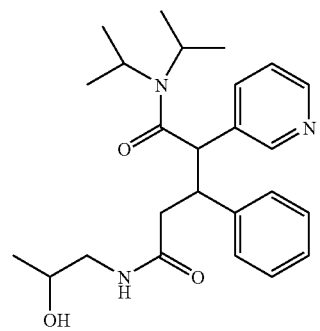

SCHEME III

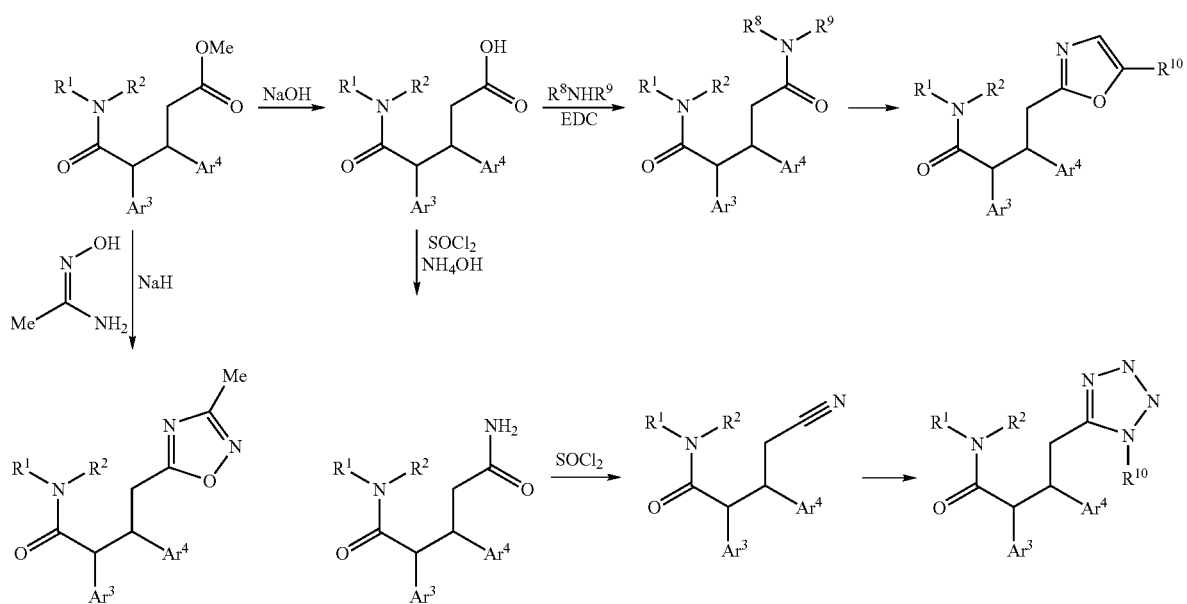

wherein
R$^8$ is hydrogen or —C$_{1-6alkyl}$,
R$^9$ is hydrogen, —C$_{0-6}$alkylene-A, —C$_{1-6}$alkyl, or —NH$_2$,
R$^{10}$ is hydrogen or —C$_{1-6}$alkyl,
and R$^1$, R$^2$, Ar$^3$, Ar$^4$, and A are as previously defined.

Example III-1

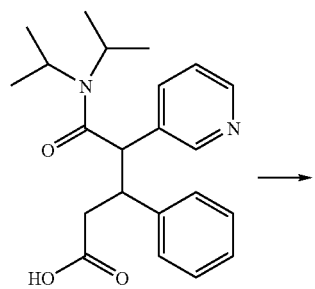

N$^5$-(2-hydroxypropyl)-N$^1$,N$^1$-diisopropyl-3-phenyl-2-pyridin-3-ylpentanediamide To a mixture of 5-(diisopropylamino)-5-oxo-3-phenyl-4-pyridin-3-ylpentanoic acid (Diastereomer 2, 50 mg, 0.136 mmol), EDC (52 mg, 0.271 mmol) and HOAt (18 mg, 0.136 mmol) in 0.2 mL DMF was added Hunig's base (0.047 mL, 0.271 mmol) followed by a solution of 2-hydroxypropylamine (20 mg, 0.271 mmol) in DMF (0.6 mL). The reaction mixture was stirred at room temperature overnight, then purified directly by r.p. HPLC. The desired fractions from HPLC were combined and the product was isolated as free base by extraction from saturated aqueous sodium bicarbonate. White solid, mixture of diastereomers (1:1).

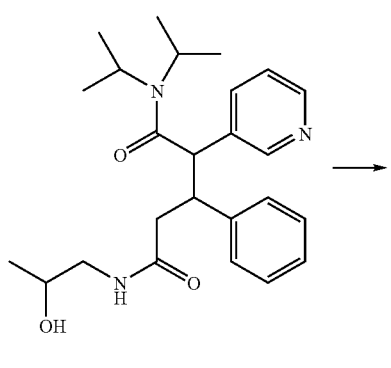

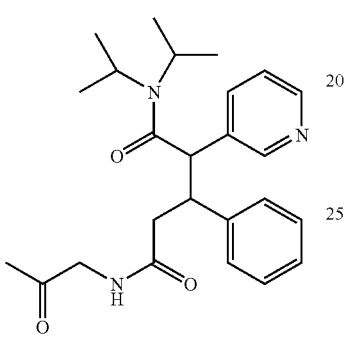

N[1],N[1]-diisopropyl-N[5]-(2-oxopropyl)-3-phenyl-2-pyridin-3-ylpentanediamide

To a cold (0° C.) suspension of N[5]-(2-hydroxypropyl)-N[1],N[1]-diisopropyl-3-phenyl-2-pyridin-3-ylpentanediamide (20 mg, 0.047 mmol) in 1 mL dry CH$_2$Cl$_2$ was added solid Dess-Martin periodinane (24 mg, 0.056 mmol), and the reaction was stirred at 0° C. for 3.5 h. The cooling bath was then removed and stirred at room temperature for 1.5 h. More Dess-Martin periodinane was added (two 24 mg portions in 1.5 h interval). The reaction was quenched with saturated aqueous NaHCO$_3$: saturated aqueous Na$_2$S$_2$O$_3$ (1:1 v/v) and partitioned between CH$_2$Cl$_2$ and saturated aqueous NaHCO$_3$. The aqueous layer was extracted with CH$_2$Cl$_2$ (3×). The combined organic layers were dried over anhydrous Na$_2$SO$_4$ and concentrated to give a white solid. This material was used directly in the next step.

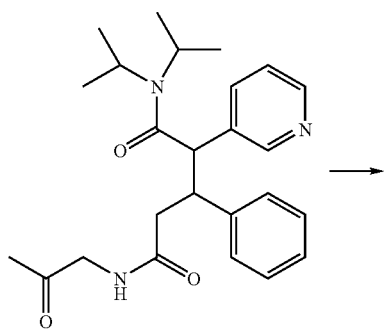

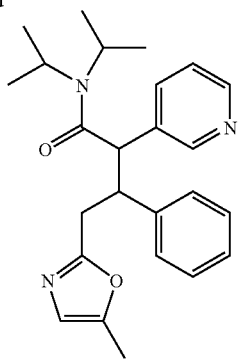

N,N-diisopropyl-4-(5-methyl-1,3-oxazol-2-yl)-3-phenyl-2-pyridin-3-ylbutanamide

To a solution of N[1],N[1]-diisopropyl-N[5]-(2-oxopropyl)-3-phenyl-2-pyridin-3-ylpentanediamide (63 mg, 0.149 mmol) in 0.7 mL pyridine was added POCl$_3$ (0.35 mL), and the mixture was heated at 70 C for 3 h. The resulting red solution was cooled to room temperature and diluted with EtOAc, then cooled to 0° C. Saturated aqueous NaHCO$_3$ solution was added slowly until the aqueous layer became basic. The aqueous layer was extracted with EtOAc (3×). The combined organic layers were dried over anhydrous Na$_2$SO$_4$ and concentrated, then purified by r.p. HPLC. The desired fractions from HPLC were combined, and the product was isolated as free base by extraction from aqueous sodium bicarbonate. White solid, single diastereomer.

$^1$H NMR (500 MHz, CDCl$_3$): δ 8.29-8.28 (m, 1H), 8.12 (d, J=2.2 Hz, 1H), 7.59 (d, J=8.1 Hz, 1H), 7.07-6.98 (m, 4H), 6.90 (d, J=7.1 Hz, 2H), 6.45 (s, 1H), 4.18-4.11 (m, 2H), 4.04-3.99 (m, 1H), 3.40-3.29 (m, 2H), 3.24-3.19 (m, 1H), 2.17 (s, 3H), 1.46 (d, J=6.6 Hz, 3H), 1.34 (d, J=6.8 Hz, 3H), 1.25 (d, J=6.6 Hz, 3H), 0.74 (d, J=6.1 Hz, 3H). HRMS: observed, 406.2471; calculated, 406.2489.

Example III-2

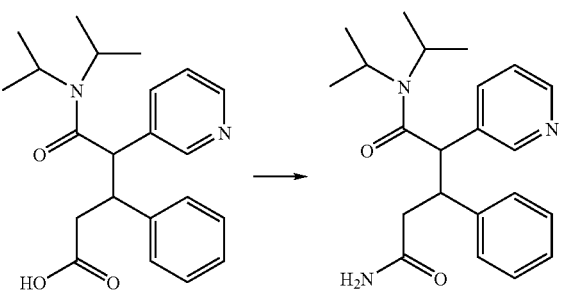

N[1],N[1]-diisopropyl-3-phenyl-2-pyridin-3-ylpentanediamide 5-(diisopropylamino)-5-oxo-3-phenyl-4-pyridin-3-ylpentanoic acid (Diastereomer 2, 100 mg, 0.271 mmol) was taken in a r.b. flask and cooled to 0° C. SOCl$_2$ (2 mL) was added, and the reaction was stirred at 0° C. for 1.5 h, then concentrated and azeotroped from benzene. The resulting white solid (acid chloride) was dried under vacuum. To this acid chloride was added concentrated aqueous NH₄OH, and the resulting mixture was stirred at room temperature for 4 h, then partitioned between CH₂Cl₂ and saturated aqueous NaHCO₃. The aqueous layer was extracted with CH₂Cl₂ (3×). The combined organic layers were dried over anhydrous Na₂SO₄ and concentrated to give a white solid. This material was used directly in the next step.

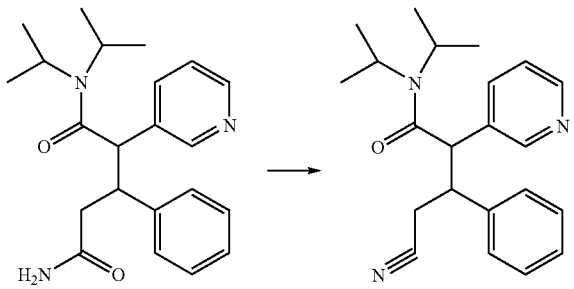

4-cyano-N,N-diisopropyl-3-phenyl-2-pyridin-3-ylbutanamide

To a solution of N¹,N¹-diisopropyl-3-phenyl-2-pyridin-3-ylpentanediamide (90 mg, 0.245 mmol) in 1 mL DMF was added SOCl₂ (0.5 mL) and heated at 90 C for 45 min. Concentrated (azeotroped 2× from benzene) and purified by r.p. HPLC. Desired fractions from HPLC were combined and the product was isolated as free base. White solid, single diastereomer.

¹H NMR (500 MHz, CDCl₃): δ 8.34 (dd, J=4.9, 1.7 Hz, 1H), 8.16 (d, J=2.2 Hz, 1H), 7.52-7.50 (m, 1H), 7.20-7.12 (m, 3H), 7.11-7.08 (m, 3H), 4.19 (d, J=10.7 Hz, 1H), 4.16-4.09 (m, 1H), 3.70-3.66 (m, 1H), 3.40-3.32 (m, 1H), 3.23 (dd, J=16.9, 7.6 Hz, 1H), 2.77 (dd, J=17.1, 2.9 Hz, 1H), 1.51 (d, J=6.6 Hz, 3H), 1.35 (d, J=6.8 Hz, 3H), 1.30 (d, J=6.8 Hz, 3H), 0.69 (d, J=6.6 Hz, 3H). HRMS: observed, 350.2222; calculated, 350.2227.

Example III-3

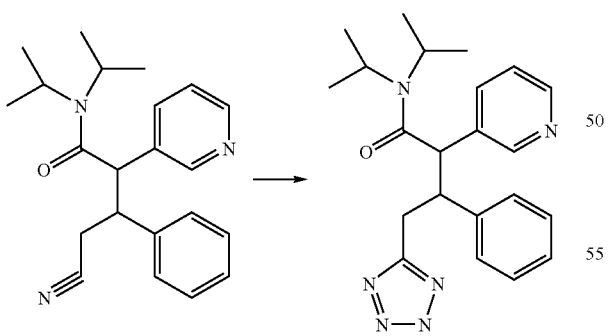

N,N-diisopropyl-3-phenyl-2-pyridin-3-yl-4-(2H-tetrazol-5-ylbutanamide

A mixture of 4-cyano-N,N-diisopropyl-3-phenyl-2-pyridin-3-ylbutanamide (Diastereomer 1, prepared using the procedures of Example III-2, starting with diastereomer 1, 20 mg, 0.057 mmol), aqueous NaN₃ (2 M, 1 mL) and aqueous ZnBr₂ (2 M, 0.5 mL) was heated at 185° C. for 20 min in a microwave reactor. The reaction mixture was then partitioned between CH₂Cl₂ and saturated aqueous NH₄Cl. The aqueous layer was extracted with CH₂Cl₂ (5×). The combined organic layers were dried over anhydrous Na₂SO₄ and concentrated, then purified by r.p. HPLC. The product was isolated as its TFA salt. Single diastereomer.

¹H NMR (500 MHz, CDCl₃): δ 9.10 (s, 1H), 8.69 (d, J=7.6 Hz, 1H), 8.54 (d, J=5.6 Hz, 1H), 7.73 (dd, J=7.8, 5.9 Hz, 1H), 7.36 (d, J=7.3 Hz, 2H), 7.32-7.29 (m, 2H), 7.25-7.22 (m, 1H), 4.65 (d, J=10.7 Hz, 1H), 4.31-4.26 (m, 1H), 4.08-4.03 (m, 1H), 3.29 (d, J=7.1 Hz), 3.25-3.11 (m, 1H), 1.09 (d, J=6.8 Hz, 3H), 0.95 (d, J=6.6 Hz, 3H), 0.90 (d, J=6.8 Hz, 3H), 0.74 (d, J=6.4 Hz, 3H). HRMS: observed, 393.2402; calculated, 393.2398.

Example III-4, III-5

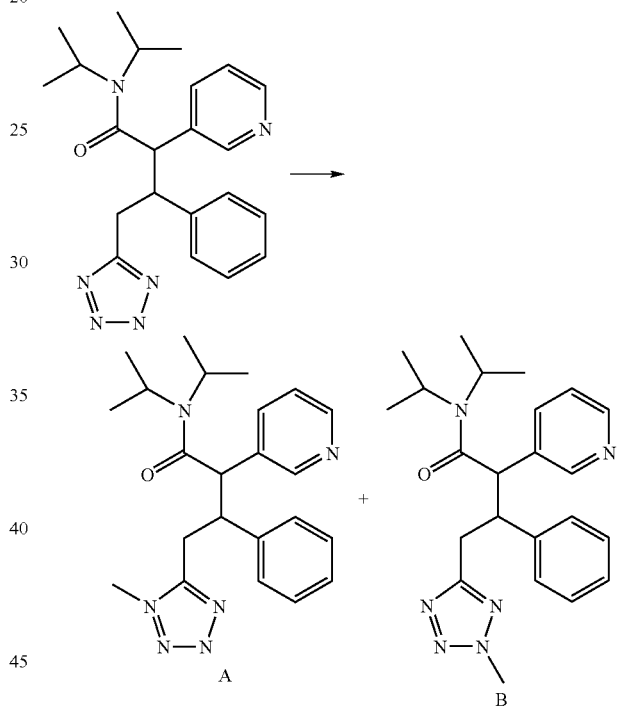

N,N-diisopropyl-4-(1-methyl-1H-tetrazol-5-yl)-3-phenyl-2-pyridin-3-ylbutanamide and N,N-diisopropyl-4-(2-methyl-2H-tetrazol-5-yl)-3-phenyl-2-pyridin-3-ylbutanamide N,N-diisopropyl-3-phenyl-2-pyridin-3-yl-4-(2H-tetrazol-5-yl)butanamide (TFA-salt) was dissolved in a mixture of MeOH (0.5 mL) and CH₂Cl₂ (1 mL). The resulting solution was cooled to 0° C. and treated with TMS-diazomethane solution (2 M in hexanes, 0.089 mL). The reaction was stirred at 0° C. for 3.5 h and then concentrated and purified by r.p. HPLC. Two regioisomers were separated and isolated as TFA salts. Regioisomer-A: white solid. Regioisomer-B: white solid.

Regioisomer-A: ¹H NMR (500 MHz, CD₃OD): δ 9.08-9.07 (m, 1H), 8.74-8.73 (m, 1H), 8.67-8.65 (m, 1H), 7.92-7.89 (m, 1H), 7.35-7.22 (m, 5H), 4.93 (d, J=11.2 Hz, 1H), 4.42-4.37 (m, 1H), 3.51 (s, 3H), 3.25-3.13 (m, 2H), 2.92 (dd, J=15.1, 4.6 Hz, 1H), 1.12 (d, J=6.8 Hz, 3H), 0.98-0.94 (m, 6H), 0.83 (d, J=6.8 Hz, 3H). HRMS: observed, 407.2537; calculated, 407.2554.

Regioisomer-B: $^1$H NMR (500 MHz, CD$_3$OD): δ 9.05 (s, 1H), 8.72-8.67 (m, 2H), 7.92-7.89 (m, 1H), 7.35 (d, J=7.1 Hz, 2H), 7.25 (t, J=7.3 Hz, 2H), 7.19-7.16 (m, 1H), 4.83 (s, 1H), 4.36-4.31 (m, 1H), 4.13 (s, 3H), 4.11-4.07 (m, 1H), 3.24-3.17 (m, 2H), 2.87 (dd, J=14.9, 5.1 Hz, 1H), 1.11 (d, J=6.6 Hz, 3H), 0.97 (d, J=6.6 Hz, 3H), 0.88 (d, J=6.8 Hz, 3H), 0.83 (d, J=6.4 Hz, 3H). HRMS: observed, 407.2533; calculated, 407.2554.

Example III-6

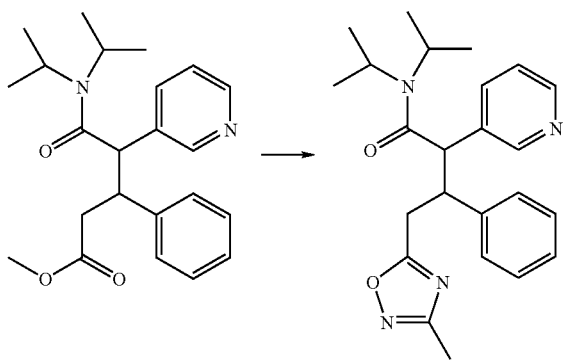

N,N-diisopropyl-4-(3-methyl-1,2,4-oxadiazol-5-yl)-3-phenyl-2-pyridin-3-ylbutanamide A mixture of acetamide oxime (23 mg, 0.314 mmol), NaH (8 mg, 0.314 mmol) and 4 A powdered molecular sieves in 2 mL dry THF was heated at 60° C. for 1 h and then cooled to room temperature. To this mixture was added a solution of methyl 5-(diisopropylamino)-5-oxo-3-phenyl-4-pyridin-3-ylpentanoate (Diastereomer 1, 100 mg, 0.261 mmol) in THF (1 mL). The mixture was heated at 60° C. for 2 h and then cooled to room temperature and filtered through a pad of celite (THF wash). The combined washings and filtrate were concentrated. The residue was then partitioned between CH$_2$Cl$_2$ and water. The aqueous layer was extracted with CH$_2$Cl$_2$ (3×). The combined organic layers were dried over anhydrous Na$_2$SO$_4$ and concentrated, then purified by r.p. HPLC. The desired fractions from HPLC were combined, and the product was isolated as a free base by extraction from aqueous sodium bicarbonate. White solid. Single diastereomer.

$^1$H NMR (500 MHz, CDCl$_3$): δ 8.63 (d, J=2.2 Hz, 1H), 8.56-8.55 (m, 1H), 8.05-8.03 (m, 1H), 7.33-7.31 (m, 1H), 7.27-7.23 (m, 4H), 7.19-7.16 (m, 1H), 4.22-4.03 (m, 3H), 3.13-3.06 (m, 1H), 3.03-2.98 (m, 1H), 2.95-2.91 (m, 1H), 2.21 (s, 3H), 1.17 (d, J=6.6 Hz), 0.93-0.89 (m, 6H), 0.85 (d, J=6.6 Hz, 3H). HRMS: observed, 407.2423; calculated, 407.2442.

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward K$^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at Hz. A Kv1.5 blocker may also display use-dependence, during which the block of the outward K$^+$ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the 10$^{th}$ pulse than for the 1$^{st}$ pulse of the train. A Kv1.5 blocker may exhibit both use-dependence and rate-dependence.

A Kv1.5 blocker may also be identified through electrophysiological studies of native I$_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135, 2003) and Schroeder et al. (J. of Biomol. Screen., 8(1); 50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 µg/ml streptomycin, 1000 µg/ml G-418 sulfate. Cells are subcultured by treatment with Versene, then suspended in phosphate-buffered saline (PBS) and centrifuged The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxylethylpiperazine-N$^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, K$_3$PO$_4$ 1.47, MgCl$_2$ 0.50, NaCl 138, Na$_3$PO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS ~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 µL of external buffer.
2. Planar micropipette hole resistances (Rp) is determined by applying a 10 mV, 160 ms potential difference across each hole (Hole test).

3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the 27$^{th}$ depolarization to +40 mV (in the 5 Hz train) is plotted as a function of antagonist concentration. The concentrations of drug required to inhibit current by 50% (IC$_{50}$) are determined by fitting of the Hill equation to the concentration response data: % of Control=100× $(1+([Drug]/IC_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the 1$^{st}$ depolarization to +40 mV minus the pre-compound mean current amplitude during the 27$^{th}$ depolarization to +40 mV)
4) peak current (maximum current amplitude during the 27$^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide >20% inhibition at a concentration of 33 μM or less in the high throughput Kv1.5 planar patch clamp assay described above.

Atomic Absorption Spectroscopy Protocol:

This assay identifies agents that specifically block the human Kv1.5 K+ channel heterologously expressed in CHO cells as measured by Rb$^+$ efflux using Flame Atomic Absorption Spectroscopy (FAAS). The application of FAAS for measuring ion channel activity was adapted from Terstappen et al, *Anal. Biochem.*, 272:149-155, 1999. CHO cells expressing human Kv1.5 are cultured as described above, then harvested with trypsin-EDTA and washed with medium.

1. 40,000 cells per well are seeded in a 96-well cell culture plate (assay plate) and the cells are allowed to grow for 48 hours at 37° C.
2. The medium is removed and 200 μl of Rb Load Buffer (Aurora Biomed, Vancouver, BC) is added for 3 hours at 37-C under 5% CO$_2$.
3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1−(A−B)/(C−B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide >25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Compounds of the invention may optionally be administered to a patient in need of Kv1.5 inhibition by means of coronary stent placement in the patient. The stent may include the compound by any standard means known to persons skilled in the art, e.g., coating or other means for associating the compound to the stent surface, or impregnating the compound into the stent. Such stents may be used in both intrapericardial administration and intracardiac administration by means of a catheter or other device that monitors rhythm.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbuminne, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppressant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:
1. A compound selected from the group consisting of:
N,N-diisopropyl-3-phenyl-4-[(4-phenylbutanoyl)amino]-2-pyridin-3-ylbutanamide,
N,N-diisopropyl-3-phenyl-4-[({[(1S)-1-phenylethyl]amino}carbonyl)amino]-2-pyridin-3-ylbutanamide,
N,N-diisopropyl-3-phenyl-4-[(3-phenylpropanoyl)amino]-2-pyridin-3-ylbutanamide,
4-{([3-(2-fluorophenyl)propanoyl]amino}-N,N-diisopropyl-3-phenyl-2-pyridin-3-ylbutanamide,
N,N-diisopropyl-3-phenyl-4-[(3-phenylbutanoyl)amino]-2-pyridin-3-ylbutanamide,
N,N-diisopropyl-4-({[(3-methylbenzyl)amino]carbonyl}amino)-3-phenyl-2-pyridin-3-ylbutanamide,
4-({[(4-bromobenzyl)amino]carbonyl}amino)-N,N-diisopropyl-3-phenyl-2-pyridin-3-ylbutanamide,
4-({[(4-fluorobenzyl)amino]carbonyl}amino)-N,N-diisopropyl-3-phenyl-2-pyridin-3-ylbutanamide,
N,N-diisopropyl-3-phenyl-4-[({[(1R,2S)-2-phenylcyclopropyl]amino}carbonyl)amino]-2-pyridin-3-ylbutanamide,
N,N-diisopropyl-4-[({[1-(1-naphthyl)ethyl]amino}carbonyl)amino]-3-phenyl-2-pyridin-3-ylbutanamide,
4-({[(3-fluorobenzyl)amino]carbonyl}amino)-N,N-diisopropyl-3-phenyl-2-pyridin-3-ylbutanamide,
4-[(benzylsulfonyl)amino]-N,N-diisopropyl-3-phenyl-2-pyridin-3-ylbutanamide,
N,N-diisopropyl-4-({[(4-methylbenzyl)amino]carbonyl}amino)-3-phenyl-2-pyridin-3-ylbutanamide,
4-({[(2-fluorobenzyl)amino]carbonyl}amino)-N,N-diisopropyl-3-phenyl-2-pyridin-3-ylbutanamide,
N,N-diisopropyl-3-phenyl-4-{[(2-phenyl-1,3-thiazol-4-yl)acetyl]amino}-2-pyridin-3-ylbutanamide,
4-{[3-(2-chlorophenyl)propanoyl]amino}-N,N-diisopropyl-3-phenyl-2-pyridin-3-ylbutanamide,
N,N-diisopropyl-4-({[(4-methoxybenzyl)amino]carbonyl}amino)-3-phenyl-2-pyridin-3-ylbutanamide,
N,N-diisopropyl-3-phenyl-4-({[(E)-2-phenylvinyl]sulfonyl}amino)-2-pyridin-3-ylbutanamide,
N,N-diisopropyl-3-phenyl-2-pyridin-3-yl-4-({[2-(trifluoromethyl)phenyl]sulfonyl}amino)butanamide,
N,N-diisopropyl-3-phenyl-2-pyridin-3-yl-4-[(3-pyridin-2-ylpropanoyl)amino]butanamide,
N,N-diisopropyl-3-phenyl-4-({[(2-phenylethyl)amino]carbonyl}amino)-2-pyridin-3-ylbutanamide,
4-({[(2-chlorobenzyl)amino]carbonyl}amino)-N,N-diisopropyl-3-phenyl-2-pyridin-3-ylbutanamide,
4-{[(cyclohexylamino)carbonyl]amino}-N,N-diisopropyl-3-phenyl-2-pyridin-3-ylbutanamide,
4-({[(3-fluorophenyl)amino]carbonyl}amino)-N,N-diisopropyl-3-phenyl-2-pyridin-3-ylbutanamide,
N,N-diisopropyl-4-{[(1-naphthylamino)carbonyl]amino}-3-phenyl-2-pyridin-3-ylbutanamide,
N,N-diisopropyl-3-phenyl-4-[({[(1R)-1-phenylethyl]amino}carbonyl)amino]-2-pyridin-3-ylbutanamide,
4-({[(diphenylmethyl)amino]carbonyl}amino)-N,N-diisopropyl-3-phenyl-2-pyridin-3-ylbutanamide,
N,N-diisopropyl-3-phenyl-4-[({[(1S)-1-phenylethyl]amino}carbonyl)amino]-2-pyridin-3-ylbutanamide,
4-{[(sec-butylamino)carbonyl]amino}-N,N-diisopropyl-3-phenyl-2-pyridin-3-ylbutanamide,
4-({[(diphenylmethyl)amino]carbonyl}amino)-N,N-diisopropyl-3-phenyl-2-pyridin-3-ylbutanamide,
4-[(2,3-dihydro-1H-inden-2-ylacetyl)amino]-N,N-diisopropyl-3-phenyl-2-pyridin-3-ylbutanamide,
4-(acetylamino)-N,N-diisopropyl-3-phenyl-2-pyridin-3-ylbutanamide,
N,N-diisopropyl-3-phenyl-2-pyridin-3-yl-4-({[2-(trifluoromethyl)phenyl]acetyl}amino)butanamide,
4-{[(2-chloro-6-fluorophenyl)acetyl]amino}-N,N-diisopropyl-3-phenyl-2-pyridin-3-ylbutanamide,
N-[4-(diisopropylamino)-4-oxo-2-phenyl-3-pyridin-3-ylbutyl]pentanamide,
N,N-diisopropyl-4-{[3-(1-methyl-1H-pyrazol-4-yl)propanoyl]amino}-3-phenyl-2-pyridin-3-ylbutanamide,
methyl 5-{[2-(1,3-benzodioxol-5-yl)ethyl]amino}-5-oxo-3-phenyl-4-pyridin-3-ylpentanoate,
$N^5$-(2-fluorobenzyl)-$N^1$,$N^1$-diisopropyl-3-phenyl-2-pyridin-3-ylpentanediamide,
$N^1$,$N^1$-diisopropyl-3-phenyl-$N^5$-(3-phenylpropyl)-2-pyridin-3-ylpentanediamide,
$N^1$,$N^1$-diisopropyl-3-phenyl-$N^5$-(1-phenylethyl)-2-pyridin-3-ylpentanediamide,
$N^5$-[2-(tert-butylthio)ethyl]-$N^1$,$N^1$-diisopropyl-3-phenyl-2-pyridin-3-ylpentanediamide,
$N^1$,$N^1$-diisopropyl-3-phenyl-$N^5$-(2-phenylethyl)-2-pyridin-3-ylpentanediamide,
$N^5$-(2,3-dihydro-1H-inden-2-yl)-$N^1$,$N^1$-diisopropyl-3-phenyl-2-pyridin-3-ylpentanediamide,
$N^1$,$N^1$-diisopropyl-3-phenyl-$N^5$-[(4-phenylmorpholin-2-yl)methyl]-2-pyridin-3-ylpentanediamide,
$N^1$,$N^1$-diisopropyl-3-phenyl-$N^5$-pyridin-2-yl-2-pyridin-3-ylpentanediamide,
$N^1$,$N^1$-diisopropyl-$N^5$-(1-isopropyl-2-methylpropyl)-3-phenyl-2-pyridin-3-ylpentanediamide,
$N^5$-(1H-benzimidazol-2-ylmethyl)-$N^1$,$N^1$-diisopropyl-3-phenyl-2-pyridin-3-ylpentanediamide,
$N^5$-(3-isopropoxypropyl)-$N^1$,$N^1$-diisopropyl-3-phenyl-2-pyridin-3-ylpentanediamide,
$N^1$,$N^1$-diisopropyl-3-phenyl-2-pyridin-3-yl-N-5-(pyridin-2-ylmethyl)pentanediamide,
methyl 5-{[5-(diisopropylamino)-5-oxo-3-phenyl-4-pyridin-3-ylpentanoyl]amino}pentanoate,
1-tert-butyl 5-methyl 3-phenyl-2-pyridin-3-ylpentanedioate,
methyl 4-(3-cyanophenyl)-5-(diisopropylamino)-5-oxo-3-pyridin-3-ylpentanoate,
methyl 4-(3-bromophenyl)-5-(diisopropylamino)-5-oxo-3-pyridin-3-ylpentanoate,
$N^1$,$N^1$-diisopropyl-$N^5$,$N^5$-dimethyl-3-phenyl-2-pyridin-3-ylpentanediamide,
$N^1$,$N^1$-diisopropyl-$N^5$-methyl-3-phenyl-2-pyridin-3-ylpentanediamide,
methyl 5-(diisopropylamino)-5-oxo-4-pyridin-3-yl-3-pyridin-4-ylpentanoate,
5-methoxy-5-oxo-3-phenyl-2-pyridin-3-ylpentanoic acid,
methyl 5-(diisopropylamino)-5-oxo-4-pyridin-3-yl-3-pyridin-4-ylpentanoate,
methyl 5-(diisopropylamino)-5-oxo-3-phenyl-4-pyridin-2-ylpentanoate,
methyl 5-(diisopropylamino)-5-oxo-4-pyridin-2-yl-3-pyridin-4-ylpentanoate,
methyl 5-(diisopropylamino)-5-oxo-3,4-dipyridin-4-ylpentanoate,
methyl 5-(diisopropylamino)-5-oxo-4-phenyl-3-pyridin-4-ylpentanoate,
methyl 5-(diisopropylamino)-5-oxo-3-phenyl-4-pyridin-4-ylpentanoate,
3-(3-cyanophenyl)-4-({[(2-fluorobenzyl)amino]carbonyl}amino)-N,N-diisopropyl-2-pyridin-3-ylbutanamide,

N-[4-(diisopropylamino)-4-oxo-2-phenyl-3-pyridin-3-yl-butyl]-2-fluoro-N-(methylsulfonyl)phenylalaninamide,
N-[4-(diisopropylamino)-4-oxo-2-phenyl-3-pyridin-3-yl-butyl]-2-fluorophenylalaninamide,
N-(tert-butoxycarbonyl)-N-[4-(diisopropylamino)-4-oxo-2-phenyl-3-pyridin-3-ylbutyl]-2-fluorophenylalaninamide,
N,N-diisopropyl-4-(5-methyl-1,2,4-oxadiazol-3-yl)-3-phenyl-2-pyridin-3-ylbutanamide,
N,N-diisopropyl-4-(2-methyl-2H-tetrazol-5-yl)-3-phenyl-2-pyridin-3-ylbutanamide,
N,N-diisopropyl-4-(1-methyl-1H-tetrazol-5-yl)-3-phenyl-2-pyridin-3-ylbutanamide,
5-hydrazino-N,N-diisopropyl-5-oxo-3-phenyl-2-pyridin-3-ylpentanamide,
N,N-diisopropyl-4-(3-methyl-1,2,4-oxadiazol-5-yl)-3-phenyl-2-pyridin-3-ylbutanamide,
N,N-diisopropyl-4-(5-methyl-1,3-oxazol-2-yl)-3-phenyl-2-pyridin-3-ylbutanamide,
4-cyano-N,N-diisopropyl-3-phenyl-2-pyridin-3-ylbutanamide,
N,N-diisopropyl-4-[(methylsulfonyl)amino]-3-phenyl-2-pyridin-3-ylbutanamide,
N,N-diisopropyl-4-(5-methyl-1,3-oxazol-2-yl)-3-phenyl-2-pyridin-3-ylbutanamide,
5-hydroxy-N,N-diisopropyl-3-phenyl-2-pyridin-3-ylpentanamide,
tert-butyl 4-(diisopropylamino)-4-oxo-2-phenyl-3-pyridin-3-ylbutylcarbamate,
methyl 3-(3-cyanophenyl)-5-(diisopropylamino)-5-oxo-4-pyridin-3-ylpentanoate,
methyl 3-(3-bromophenyl)-5-(diisopropylamino)-5-oxo-4-pyridin-3-ylpentanoate,
5-(diisopropylamino)-5-oxo-3-phenyl-4-pyridin-3-ylpentanoic acid,
$N^1,N^1$-diisopropyl-3-phenyl-2-pyridin-3-ylpentanediamide,
methyl 5-(diisopropylamino)-5-oxo-4-phenyl-3-pyridin-3-ylpentanoate,
methyl 5-(diisopropylamino)-5-oxo-4-pyridin-2-yl-3-pyridin-3-ylpentanoate,
methyl 5-(diisopropylamino)-5-oxo-4-pyridin-2-yl-3-pyridin-3-ylpentanoate,
methyl 5-(diisopropylamino)-5-oxo-4-phenyl-3-pyridin-3-ylpentanoate,
methyl 5-(diisopropylamino)-5-oxo-3-phenyl-4-pyridin-3-ylpentanoate,
methyl 5-(diisopropylamino)-5-oxo-3,4-dipyridin-3-ylpentanoate,
methyl 5-(diisopropylamino)-3-(6-methoxypyridin-3-yl)-5-oxo-4-phenylpentanoate,
methyl 5-(diisopropylamino)-5-oxo-3-pyridin-2-yl-4-pyridin-4-ylpentanoate,
methyl 5-(diisopropylamino)-5-oxo-3-pyridin-2-yl-4-pyridin-3-ylpentanoate,
methyl 5-(diisopropylamino)-5-oxo-3,4-dipyridin-2-ylpentanoate, and
methyl 5-(diisopropylamino)-5-oxo-4-phenyl-3-pyridin-2-ylpentanoate, or a pharmaceutically acceptable salt thereof.

2. A pharmaceutical formulation comprising a pharmaceutically acceptable carrier and the compound of claim 1.

3. A pharmaceutical composition made by combining the compound of claim 1 and a pharmaceutically acceptable carrier.

4. A method of treating cardiac arrythmia comprising administering a compound of claim 1 with a compound selected from one of the classes of compounds consisting of antiarrhythmic agents having Kv1.5 blocking activities, ACE inhibitors, angiotensin II antagonists, cardiac glycosides, L-type calcium channel blockers, T-type calcium channel blockers, selective and nonselective beta blockers, endothelin antagonists, thrombin inhibitors, aspirin, nonselective NSAIDs, warfarin, factor Xa inhibitors, low molecular weight heparin, unfractionated heparin, clopidogrel, ticlopidine, IIb/IIIa receptor antagonists, 5HT receptor antagonists, integrin receptor antagonists, thromboxane receptor antagonists, TAFI inhibitors and P2T receptor antagonists.

* * * * *